(12) United States Patent
Ciani et al.

(10) Patent No.: US 10,751,329 B2
(45) Date of Patent: Aug. 25, 2020

(54) TREATMENT OF CDKL5 DISORDERS WITH GSK3β INHIBITOR TIDEGLUSIB

(71) Applicant: Alma Mater Studiorum—Universitá di Bologna, Bologna (IT)

(72) Inventors: Elisabetta Ciani, Bologna (IT); Claudia Fuchs, Bologna (IT)

(73) Assignee: Alma Mater Studiorum—Universitádi Bologna, Bologna (IT)

( * ) Notice: Subject to any disclaimer, the term of this patent is extended or adjusted under 35 U.S.C. 154(b) by 0 days.

(21) Appl. No.: 16/083,016

(22) PCT Filed: Mar. 10, 2017

(86) PCT No.: PCT/IB2017/000239
§ 371 (c)(1),
(2) Date: Sep. 7, 2018

(87) PCT Pub. No.: WO2017/153834
PCT Pub. Date: Sep. 14, 2017

(65) Prior Publication Data
US 2019/0091207 A1    Mar. 28, 2019

Related U.S. Application Data

(60) Provisional application No. 62/306,300, filed on Mar. 10, 2016, provisional application No. 62/406,151, filed on Oct. 10, 2016.

(51) Int. Cl.
*A61K 31/433* (2006.01)
*A61P 25/00* (2006.01)

(52) U.S. Cl.
CPC ............ *A61K 31/433* (2013.01); *A61P 25/00* (2018.01)

(58) Field of Classification Search
CPC .................................................... A61K 31/433
See application file for complete search history.

(56) References Cited

U.S. PATENT DOCUMENTS 8,158,661 B2 *   4/2012   Medina Padilla ... C07D 417/04
514/361

OTHER PUBLICATIONS

Fuchs et al. Neurobiology of Disease, 2015, 82: 298-310.*

* cited by examiner

*Primary Examiner* — Rei Tsang Shiao
(74) *Attorney, Agent, or Firm* — Servilla Whitney LLC

(57) ABSTRACT

Provided herein are methods of treating a CDKL5 deficiency with tideglusib or a derivative thereof.

16 Claims, 30 Drawing Sheets
Specification includes a Sequence Listing.

A
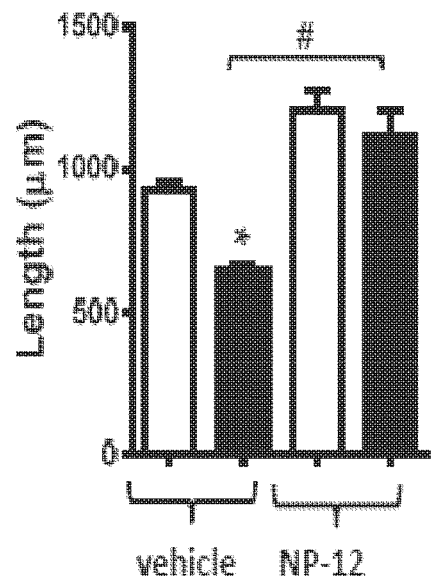
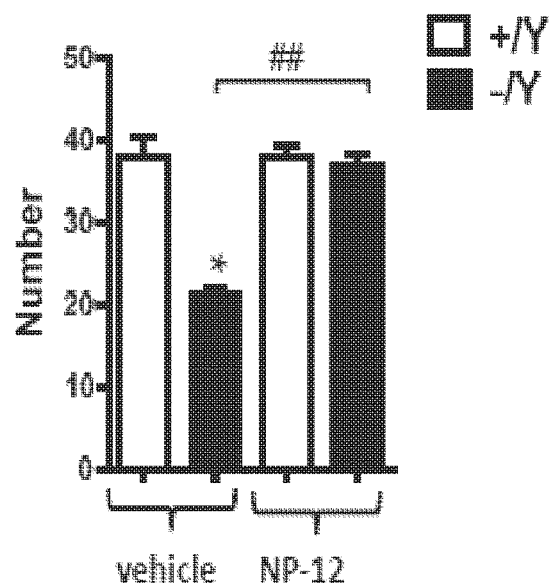
B
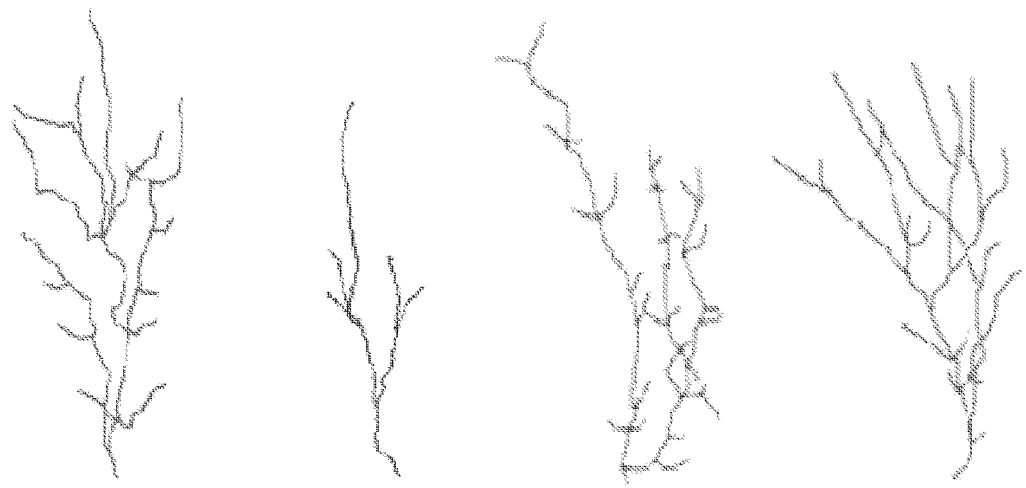
FIGS. 11A-11B

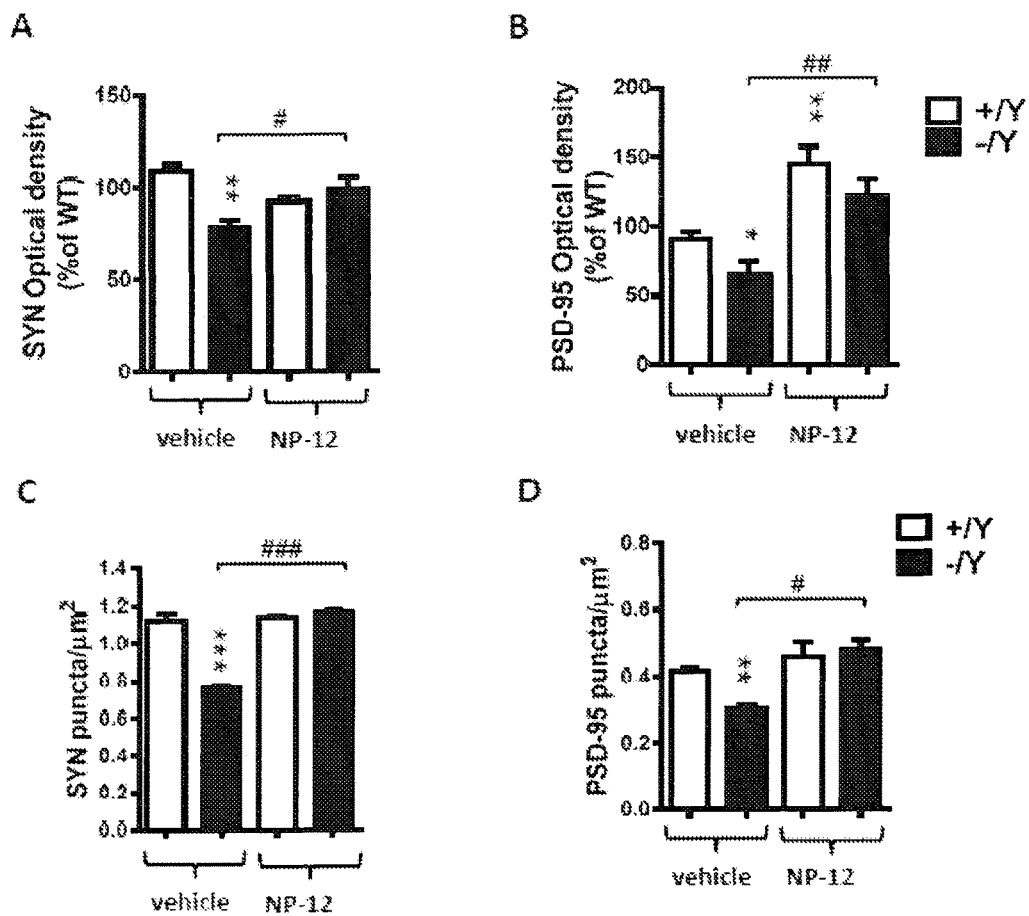
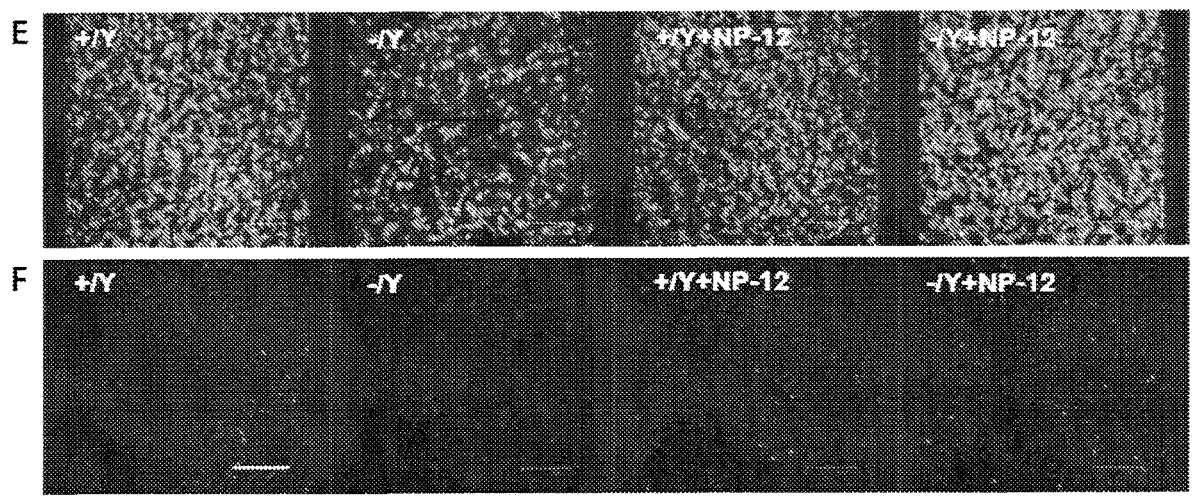
FIGS. 13A-13F

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
acgatagaaa tagaggatca accc                                          24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cccaagtata cccctttcca                                               20

<210> SEQ ID NO 3
<211> LENGTH: 18

```
<212> TYPE: DNA
<213> ORGANISM: Artificial Sequence
<220> FEATURE:
<223> OTHER INFORMATION: Primer

<400> SEQUENCE: 3
ctgtgactag gggctaga                                              18
```

TREATMENT OF CDKL5 DISORDERS WITH GSK3β INHIBITOR TIDEGLUSIB

CROSS-REFERENCE TO RELATED APPLICATIONS

This application is the National Stage entry of PCT/IB2017/000239, filed on Mar. 10, 2017, which claims priority to U.S. Application Nos. 62/306,300, filed on Mar. 10, 2016 and 62/406,151, filed on Oct. 10, 2016 which are incorporated herein by reference in their entireties.

BACKGROUND

Cyclin-dependent kinase-like 5 (CDKL5) mutation/deficiency, also known as atypical Rett syndrome, is a debilitating postnatal neurological disorder that occurs worldwide in 1 of every 17,000 to 38,000 female births. Males are also affected at a lower incidence. This disorder is not limited to ethnic or racial origin. Symptoms of CDKL5 mutation/deficiency range from mild to severe and present as early onset seizure, cognitive disability, hypotonia as well as autonomic, sleep and gastrointestinal disturbances. Symptoms of disease result from the deficiency of a functional CDKL5 protein.

Mutations in the X-linked CDKL5 gene or deficiencies in the CDKL5 protein in individuals are implicated in the development of atypical or congenital Rett syndrome. See Bertani et al., J. biol. Chem. 2006, 281:32048-320 56, Scala et al., J. Med. Gen., 2005. 42:103-107, and Kalscheuer et al., Am. J. Hum. Genet. 2003. 72:1401-1411. The CDKL5 gene is located on the X-chromosome and encodes a protein that is essential for normal brain development and function. CDKL5 protein is a multifunctional protein that has multiple effects in a neuronal cell. For example, CDKL5 can act as a kinase and phosphorylate MeCP2. Girls affected by the CDKL5 mutations or deficiencies typically have a normal prenatal history; irritability and drowsiness in the perinatal period; early-onset epilepsy with onset before 5 months of age, Rett-like features, including deceleration of head growth, stereotypies, poor to absent voluntary hand use, and sleep disturbances, and severe mental retardation with poor eye contact and virtually no language. See Bahi-Buisson and Bienvenu. 2012. Mol. Syndromol. 2:137-152.

Current treatments for CDKL5 mutations/deficiencies are primarily focused on managing symptoms. However, there are currently no treatments that improve the neurological outcome of subjects with CDKL5 mutations or deficiencies. As such, there exists a need for development of therapies for treating the CDKL5 mutations and deficiencies.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 11A-11B demonstrate the (A) mean total dendritic length (left histogram) and mean number of dendritic segments (right histogram) of granule cells in untreated (+/Y n=3, −/Y n=3) and treated (+/Y n=3, −/Y n=3) Cdkl5 male mice aged P45. (B) Examples of the reconstructed dendritic tree of Golgi-stained oldest granule cells of untreated and treated mice as in A. Values in A represent mean±SE. $*p<0.05$ as compared to the untreated $Cdkl5^{+/Y}$ condition; $\#p<0.05$; $\#\#p<0.005$ as compared to the untreated $Cdkl5^{-/Y}$ samples (Duncan's test after ANOVA).

FIGS. 13A-13F demonstrate the (A, B) optical density of SYN immunoreactivity (A) and PSD-95 immunoreactivity (B) in the molecular layer of the dentate gyrus (DG) of untreated (+/Y n=4, −/Y n=4) and treated (+/Y n=4, −/Y n=4) Cdkl5 male mice aged P45. (C,D) Number of puncta per µm² exhibiting SYN (C) and PSD-95 (D) immunoreactivity of the molecular layer of the DG of animals as in A. (E,F) Images, taken with the confocal microscope, of sections processed for SYN (E) and PSD-95 (F) immunofluorescence from the DG of an animal of each experimental group. Scale bar=6 µm. Values in A-D are represented as means±SD. $*p<0.05$; $p<0.01$; $*p<0.001$ as compared to the untreated $Cdkl5^{+/Y}$ condition; $\#p<0.05$; $\#\#p<0.01$; $\#\#\#p<0.001$ as compared to the untreated $Cdkl5^{-/Y}$ samples (Duncan's test after ANOVA).

FIGS. 19A-19 C show the results from A: Spatial learning assessed with the Morris water maze in untreated (+/Y n=12, −/Y n=12) and treated (+/Y n=3, −/Y n=6) Cdkl5 male mice aged P45 at the end of treatment. B,C: Passive avoidance test (PA) on untreated and treated Cdkl5 male mice as in (A). Graphs show the latency time for entering the dark compartment on the first day (A) and on the second day (B) of the behavioral procedure. Values represent mean±SE. $p<0.01$, $*p<0.001$ as compared to the untreated Cdkl5+/Y condition; $\#p<0.01$ as compared to the untreated Cdkl5−/Y condition. (Duncan's test after ANOVA).

FIGS. 21A-21B show P-GSK3β-Ser9 levels normalized to total GSK3β levels (A) and GSK3β levels normalized to glyceraldehyde-3-phosphate dehydrogenase (GAPDH) levels (B). Data are expressed as fold difference in comparison to Cdkl5+/Y mice aged P45. Values are represented as means±SE. $*p<0.05$; $**p<0.01$ as compared to the corresponding Cdkl5+/Y condition; (Duncan's test after ANOVA).

DETAILED DESCRIPTION

Figure 1:
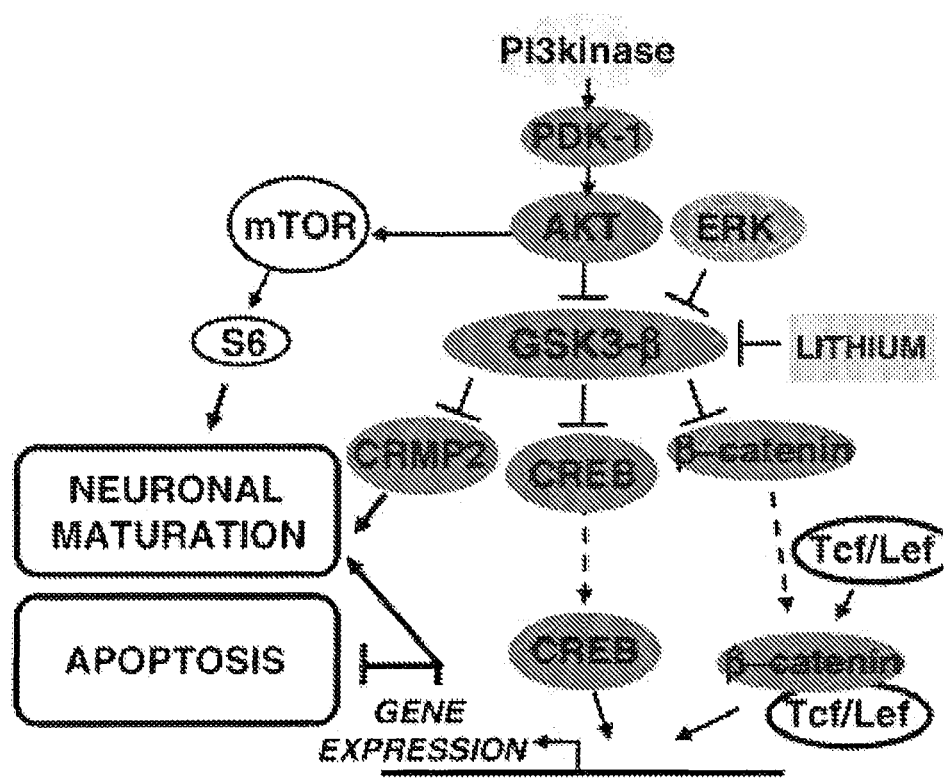
FIG. 1 shows a diagram of the AKT/GSK3 signalling pathway.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "composition" refers to a combination of active agent and at least one other compound or molecule, inert (for example, a detectable agent or label) or active, such as an adjuvant.

As used herein, "control" is an alternative subject or sample used in an experiment for comparison purpose and included to minimize or distinguish the effect of variables other than an independent variable.

As used herein, "positive control" refers to a "control" that is designed to produce the desired result, provided that all reagents are functioning properly and that the experiment is properly conducted.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "effective amount" is an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function. The term "effective amount" can refer to an amount of tideglusib or derivative thereof that can decrease the activity of GSK3β, increase neuron maturation, increase synaptic connectivity, and/or, decrease neuron death as compared to a control (e.g. a wild-type and/or untreated control) and/or a cell, tissues, and/or organ lacking CDKL5 and/or having a mutated or otherwise dysfunctional CDKL5 gene and/or protein.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

The term "least effective amount" is the least amount of a composition needed to effect the desired and/or beneficial biological, emotional, medical, therapeutic or clinical response of a cell, tissue, system, animal, or human. Thus, the "least effective amount" can be the least amount of tideglusib or derivative thereof that can decrease the activity of GSK3β, increase neuron maturation, increase synaptic connectivity, and/or, decrease neuron death as compared to a control (e.g. a wild-type and/or untreated control) and/or a cell, tissues, and/or organ lacking CDKL5 and/or having a mutated or otherwise dysfunctional CDKL5 gene and/or protein.

As used interchangeably herein, "subject," "individual," or "patient" refers to a vertebrate organism.

As used herein, "therapeutic" refers to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof. The disease or disorder can be a CDKL5 deficiency and/or Rett Syndrome.

The terms "treating" and "treatment" as used herein refer generally to obtaining a desired pharmacological and/or physiological effect. The effect may be prophylactic in terms of preventing or partially preventing a disease, symptom or condition thereof, such as disease or disorders resulting from CDKL5 mutations and/or deficiencies, the CDKL5 variant of Rett syndrome, or other CDKL5-mediated neurological disorder, and/or may be therapeutic in terms of a partial or complete cure of a disease, condition, symptom or adverse effect attributed to the disease, disorder, or condition. The term "treatment" as used herein covers any treatment of CDKL5-mediated neurological disorder in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The term "treatment" as used herein refers to both therapeutic treatment and prophylactic or preventative measures. Those in need of treatment include those already with the disorder as well as those in which the disorder is to be prevented.

As used herein, "therapeutically effective amount" refers to the amount of tideglusib or derivative thereof, a composition containing tideglusib or derivative thereof, a pharmaceutical formulation containing tideglusib or derivative thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of tideglusib or derivative thereof, a composition containing tideglusib or derivative thereof, pharmaceutical formulation containing tideglusib or derivative thereof that, when administered alone or co-administered with a secondary agent, is sufficient to prevent development of, reduce or alleviate to some extent, one or more of the symptoms of CDKL5 deficiency and/or Rett syndrome. "Therapeutically effect amount" includes the amount of tideglusib or derivative thereof, a composition containing a tideglusib or derivative thereof, a pharmaceutical formulation containing tideglusib or derivative thereof that, when administered alone or co-administered with a secondary agent, is sufficient to increase neuron survival, neuron number, neurite growth, elongation, and/or branch density in a region of the brain of a subject as compared to a control. "Therapeutically effect amount" includes the amount of the amount of tideglusib or derivative thereof, a composition containing a tideglusib or derivative thereof, a pharmaceutical formulation containing tideglusib or derivative thereof that, when administered alone or co-administered with a secondary agent, is sufficient to increase learning ability in a subject as compared to a control. "Therapeutically effect amount" includes the amount of tideglusib or derivative thereof, a composition containing a tideglusib or derivative thereof, a pharmaceutical formulation containing tideglusib or derivative thereof that, when administered alone or co-administered with a secondary agent, is sufficient to increase memory ability in a subject as compared to a control. "Therapeutically effect amount" includes the amount of tideglusib or derivative thereof, a composition containing a tideglusib or derivative thereof, a pharmaceutical formulation containing tideglusib or derivative thereof that, when administered alone or co-administered with a secondary agent, is sufficient to improve motor function in a subject as compared to a control. "Therapeutically effect amount" includes the amount of tideglusib or derivative thereof, a composition containing a tideglusib or derivative thereof, a pharmaceutical formulation containing tideglusib or derivative thereof that, when administered alone or co-administered with a secondary agent, is sufficient to restore learning ability, memory ability, and/or motor function to levels that are substantially similar to wild-type or normal levels. "Therapeutically effect amount" includes the amount of tideglusib or derivative thereof, a composition containing a tideglusib or derivative thereof, a pharmaceutical formulation containing tideglusib or derivative thereof that, when administered alone or co-administered with a secondary agent, is sufficient to restore neuron number, neuron survival, neurite growth, neurite elongation, neurite branch number, and/or neurite branch density in a region of the brain to levels that are substantially similar to wild-type or normal levels. The therapeutically effective amount will vary depending on the exact chemical structure of tideglusib or derivative thereof, the composition containing a tideglusib or derivative thereof, the pharmaceutical formulation containing tideglusib or derivative thereof, the CDKL5 deficiency, Rett syndrome or symptom thereof being treated, the route of administration, the time of administration, the rate of excretion, the drug combination, the judgment of the treating physician, the dosage form, and the age, weight, general health, sex and/or diet of the subject to be treated.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "preventative" and "prevent" refers to hindering or stopping a disease or condition before it occurs, even if undiagnosed, or while the disease or condition is still in the sub-clinical phase.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "chemotherapeutic agent" or "chemotherapeutic" refer to a therapeutic agent utilized to prevent or treat cancer.

As used herein, "matrix" refers to a material, in which one or more specialized structures, molecules, or compositions, are embedded.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "immunomodulator," refers to an agent, such as a therapeutic agent, which is capable of modulating or regulating one or more immune function or response.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "patient" refers to an organism, host, or subject in need of treatment.

As used herein, "protein" as used herein refers to a large molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function.

As used herein, "Rett syndrome variant," "variant of Rett syndrome," and the like refers to an atypical form of Rett syndrome with similar clinical signs to Rett syndrome but an unknown etiology.

As used herein, "CDKL5 mutation" refers to any change in the nucleotide sequence of the coding region of the CDKL5 protein.

As used herein, "wild-type" is the typical form of an organism, variety, strain, gene, protein, or characteristic as it occurs in nature, as distinguished from mutant forms that may result from selective breeding or transformation with a transgene or other gene mutation (such as gene deletion).

As used herein, "dose," "unit dose," or "dosage" refers to physically discrete units suitable for use in a subject, each unit containing a predetermined quantity of tideglusib or derivative thereof and/or a pharmaceutical formulation thereof calculated to produce the desired response or responses in association with its administration.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this can be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

The phrase "subject in need thereof" as used herein can refer to a subject having or suspected of having a CDKL5 mediated disorder, including a CDKL5 mediated neurologic disorder. The phrase "subject in need thereof" as used herein can also refer to a subject having one or more symptoms of a CDKL5-mediated disorder.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

Unless otherwise defined herein, all technical and scientific terms used herein have the same meaning as commonly understood by one of ordinary skill in the art.

Discussion

Mutations in the X-linked cyclin-dependent kinase-like 5 (CDKL5) gene and resulting protein have been found in individuals with a rare neurodevelopmental disorder characterized by early-onset epileptic encephalopathy. CDKL5 mutation-linked primary clinical features are severe intellectual disability and gross motor impairment. Moreover, patients manifest features overlapping with Rett syndrome, including microcephaly, hyperventilation, hand apraxia, and stereotypies. CDKL5 disorder affects primarily females due to the X-chromosome location of the CDKL5 gene. Females are heterozygous for CDKL5 deficiency and are mosaic for mutated CDKL5 gene due to random X-chromosome inactivation. Males can also be affected, although with a lower incidence, and typically have a more severe phenotype.

CDKL5 is a serine/threonine protein kinase that is highly expressed in the brain, mainly in neurons, with both a nuclear and dendrite localization. In the early postnatal period, CDKL5 brain expression exhibits a peak, suggesting its potential importance in brain maturation and function. CDKL5 knockout (KO) mice exhibit autistic-like behavior, dendritic hypotrophy, and impairment of neural circuit communication, which indicates that CDKL5 loss of function severely impairs brain development. Using this same mouse model, it was observed that CDKL5 plays a fundamental role in postnatal hippocampal neurogenesis, affecting neural precursor proliferation as well as the survival and maturation of newborn granule cells. Disruption of neurogenesis and dendritic development was associated with alterations in hippocampal-dependent cognitive performance.

Glycogen synthase kinase 3 (GSK-3β) is a ubiquitously active serine/threonine kinase which is inhibited upon phosphorylation at Ser9 by activated protein kinase B (PKB/AKT). GSK-3β (dephosphorylated at Ser9) is a regulator of many neuronal functions, including neurite outgrowth, synapse formation, neurogenesis and survival of newly-generated neurons. The AKT/GSK-3β pathway exerts its functions by modulating the activity of a wide range of substrates (FIG. 1). CDKL5 KO mice showed a disruption of AKT/GSK3β signaling in neural precursor cells, which resulted in increased GSK3β activity, as compared to wild-type mice (Fuchs et al., 2014. Neurobiol Dis. 70(100):53-68). Indeed, many proteins involved in the AKT/GSK-3β pathway are dysregulated in CDKL5 KO mice in addition to GSK3β, including PDK-1, AKT, CRMP2, CREB, and β-catenin (Fuchs 2014). Restoration of CDKL5 induced by exogenous CDKL5 expression in the CDKL5 KO neuronal precursor cells restored phosphorylation levels of AKT and GSK3β (Fuchs, 2014) In vitro, treatment of neural precursors from CDKL5 KO mice with lithium restored neuron survival and maturation in the CDKL5 KO cells (Fuchs, 2014). Lithium acts directly on GSK3β by antagonizing GSK3β kinase activity and indirectly by increasing the inhibitory phosphorylation of GSK3β.

In view of the non-selective and indirect action of lithium on other cellular signaling pathways (Kang H. J., et al. Mol. Pharmacol. 2003; 64:228-234; Pardo R., et al. J. Neurochem. 2003; 87:417-426; Sasaki T., et al. Brain Res. 2006; 1108:98-106), a contribution of additional pathways cannot be ruled out. The AKT/mTOR/S6 signaling pathway is also altered in CDKL5 KO mice (Amendola E., et al. 2014. PLoS One. 2014. May 16; 9(5):e91613 and Wang I. T., et al. Proc. Natl. Acad. Sci. U.S.A. 2012; 109:21516-21521) (FIG. 1), suggesting that CDKL5 may coordinate multiple signaling cascades downstream to AKT. It remains to be established whether these signaling cascades are directly or indirectly engaged by CDKL5 and their effect on AKT/GSK3β signaling.

Lithium was the first GSK3 inhibitor to be discovered. Lithium is a relatively weak inhibitor (IC50 is reported at about 2 mM) of GSK3β due to its direct and indirect action on GSK3β not selective for GSK3β (or GSK3α) and has several other biologic targets that result in many adverse interactions and a small therapeutic window. Further, the effect of lithium is dependent on magnesium concentration (as lithium is a competitor of magnesium). Due to these limitations of lithium, it does not show promise as a viable treatment for CDKL5 disorders.

Many other GSK3 inhibitors are known and vary with respect to chemical composition and mode of action. Generally there are 3 types of GSK3 inhibitors: (1) Metal cations; (2) ATP-competitive inhibitors, and (3) non-ATP competitive inhibitors. ATP-competitive inhibitors influence GSK3β activity by competing with ATP for the ATP binding pocket of GSK3β. Non-ATP competitive inhibitors influence GSK3β activity in other ways, such as competing with GSK3β substrates or at other sites on the GSK3β.

Recently it was observed that the maleimide compound SB216763 (SB) was observed to restore hippocampal development by restoring dendritic development, spine morphology and distribution, survival of newborn granule cells, and connectivity in CDKL5 KO mice. It is important to note that SB is an ATP-competitive inhibitor of GSK3β. Insofar as ATP is involved in many other important cellular processes, use of an ATP-competitive inhibitor is undesirable as a treatment option due to potential adverse effects it may have on other biological functions.

With that said, described herein are methods of treating a CDKL5 disorder by administering the non-ATP competitive inhibitor tideglusib or derivative thereof to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Formulations Containing Tideglusib or Derivative Thereof

Also within the scope of this disclosure are formulations containing a tideglusib (Formula 1) or derivative thereof.

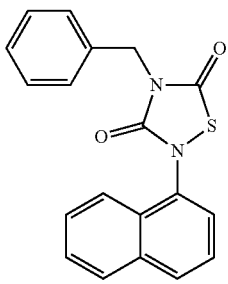

Formula 1

Tideglusib or derivative thereof can be provided to a subject in need thereof alone or as such as an active ingredient, in a pharmaceutical formulation. As such, also described herein are pharmaceutical formulations containing an amount (such as an effective, least effective, and/or therapeutically effective amount) of tideglusib or derivative thereof. In some embodiments, the pharmaceutical formulations contain a therapeutically effective amount of tideglusib or derivative thereof. The pharmaceutical formulations described herein can be administered to a subject in need thereof. The subject in need thereof can have a CDKL5 deficiency, Rett syndrome, and/or a symptom thereof. In other embodiments, the tideglusib or derivative thereof can be used in the manufacture of a medicament for the treatment and/or prevention of a CDKL5 deficiency, Rett syndrome, and/or a symptom thereof.

Pharmaceutically Acceptable Carriers and Auxiliary Ingredients and Agents

The pharmaceutical formulations containing an amount (such as an effective, least effective, and/or therapeutically effective amount) of tideglusib or derivative thereof can further include a pharmaceutically acceptable carrier. In embodiments, the tideglusib or derivative thereof is a pharmaceutically acceptable salt thereof. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition. In addition to the therapeutically effective amount of tideglusib or derivative thereof, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, prom azine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofaziimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary antiinfectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Effective Amounts of Tideglusib or Derivative Thereof and Auxiliary Agents

The pharmaceutical formulations can contain an amount, such as an effective amount, or therapeutically effective amount, of tideglusib or derivative thereof, and optionally, a therapeutically effective amount of an auxiliary agent. In some embodiments, the therapeutically effective amount of tideglusib or derivative thereof can range from about 1 µg/kg to about 10 mg/kg. In further embodiments, the therapeutically effective amount of tideglusib or derivative thereof can range from 1 ng/g bodyweight to about 0.1 mg/g bodyweight. The therapeutically effective amount of tideglusib or derivative thereof can range from about 1 pg to about 10 g. In some embodiments, the therapeutically effective mount of tideglusib or derivative thereof or pharmaceutical formulation containing the of tideglusib or derivative thereof can range from about 10 nL to about 10 mL.

For some embodiments, the therapeutically effective amount of tideglusib or derivative thereof can be from about 20 to about 50 ng per injection, such as for an intraventricular injection. In other embodiments, the therapeutically effective amount of tideglusib or derivative thereof can be about 10 microliters per injection, such as for intraventricular injection. In further embodiments, the therapeutically effective amount of tideglusib or derivative thereof can be about 5 ng/µL, such as for intraventricular injection. In yet further embodiments, the therapeutically effective amount of tideglusib or derivative thereof can be about 1.9 µg/kg of bodyweight for intraventricular injection.

In other embodiments, the therapeutically effective amount of tideglusib or derivative thereof can be from about 1 to about 2 micrograms per injection, such as for a systemically administered injection. In additional embodiments, the therapeutically effective amount of tideglusib or derivative thereof can be about 200 to about 300 µL per injection, such as for a systemically administered injection. In some embodiments, the therapeutically effective amount of tideglusib or derivative thereof can be about 5 ng/µL, such as for systemic injections For some embodiments, the therapeutically effective amount of tideglusib or derivative thereof can be about 1 to about 1.5 µg per 5 g of bodyweight. In some embodiments, the therapeutically effective amount of tideglusib or derivative thereof can be from about 200 µg to about 300 µg per kg of bodyweight.

In embodiments where there is an auxiliary active agent contained in the pharmaceutical formulation in addition to the tideglusib or derivative thereof, the therapeutically effective amount of the auxiliary active agent will vary depending on the auxiliary active agent. In some embodiments, the effective amount of the auxiliary active agent ranges from 0.001 micrograms to about 1 milligram. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of tideglusib or derivative thereof. The oral dosage form can be administered to a subject in need thereof. The oral dosage form can be formulated such that each dose administers from about 0.0001 or less to about 500 mg/kg or more bodyweight to the subject when ingested.

Where appropriate, the dosage forms described herein can be microencapsulated. The dosage form can also be prepared to prolong or sustain the release of any ingredient. In some embodiments, tideglusib or derivative thereof is the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, tideglusib or derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, tideglusib or derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of tideglusib or derivative thereof, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of tideglusib or derivative thereof, or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to tideglusib or derivative thereof, an auxiliary active ingredient, and/or pharmaceutically acceptable salt thereof, such a dosage form can contain a powder base such as lactose, glucose, trehalose, mannitol, and/or starch. In some of these embodiments, tideglusib or derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as tideglusib or derivative thereof.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, intrathecal, intravireal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of tideglusib or derivative thereof per unit dose. In an embodiment, the predetermined amount of tideglusib or derivative thereof can be a therapeutically effective amount of tideglusib or derivative thereof to treat and/or prevent a CDKL5 deficiency, Rett syndrome, and/or a symptom thereof. In other embodiments, the predetermined amount of tideglusib or derivative thereof can be an appropriate fraction of the therapeutically effective amount of the active ingredient. Such unit doses may therefore be administered once or more than once a day. Such pharmaceutical formulations may be prepared by any of the methods well known in the art.

Treatment of CDKL5-Mediated Disorders with Tideglusib or Derivatives Thereof and Formulations Thereof The tideglusib or derivatives thereof and pharmaceutical formulations thereof described herein can be used for the treatment and/or prevention of a disease, disorder, syndrome, or a symptom thereof in a subject. In some embodiments, tideglusib or derivatives thereof and pharmaceutical formulations thereof can be used to treat and/or prevent a CDKL5 deficiency, Rett syndrome, variants of Rett syndrome, and/or a symptom thereof. In some embodiments, the subject has a CDKL5 deficiency, Rett syndrome, variants of Rett syndrome, and/or a symptom thereof.

An amount of tideglusib or derivative thereof and pharmaceutical formulations thereof described herein can be administered to a subject in need thereof one or more times per day, week, month, or year. In some embodiments, the amount administered can be the therapeutically effective amount of tideglusib or derivative thereof and pharmaceutical formulations thereof. For example, tideglusib or derivative thereof and pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the tideglusib or derivative thereof and pharmaceutical formulations thereof can be administered one or more times per month, such as 1 to 5 times per month. In still further embodiments tideglusib or derivative thereof, and pharmaceutical formulations thereof can be administered one or more times per year, such as 1 to 11 times per year.

Tideglusib or derivative thereof, and pharmaceutical formulations thereof can be co-administered with a secondary agent by any convenient route. The secondary agent is a separate compound and/or formulation from the tideglusib or derivative thereof or pharmaceutical formulations thereof. The secondary agent can be administered simultaneously with the tideglusib or derivative thereof or pharmaceutical formulations thereof. The secondary agent can be administered sequentially with the tideglusib or derivative thereof or pharmaceutical formulations thereof. The secondary agent can have an additive or synergistic effect to the tideglusib or derivative thereof or pharmaceutical formulations thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, aminoacid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/ rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/ emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, vaicyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, gatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/ trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ram ucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, am ifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where tideglusib or derivative thereof or pharmaceutical formulations thereof are simultaneously co-administered with a secondary agent, tideglusib or derivative thereof or pharmaceutical formulations thereof can be administered to the subject at substantially the same time as the secondary agent. As used in this context "substantially the same time" refers to administration of tideglusib or derivative thereof or pharmaceutical formulations thereof and a secondary agent where the period of time between administration of the tideglusib or derivative thereof or pharmaceutical formulation thereof and the secondary agent is between 0 and 10 minutes.

In embodiments where tideglusib or derivative thereof or pharmaceutical formulations thereof is sequentially co-administered with a secondary agent, tideglusib or derivative thereof or pharmaceutical formulations thereof can be administered first, and followed by administration of the secondary agent after a period of time. In other embodiments where tideglusib or derivative thereof or pharmaceutical formulations thereof is sequentially co-administered with a secondary agent, the secondary agent can be administered first, and followed by administration of tideglusib or derivative thereof or pharmaceutical formulations thereof after a period of time. In any embodiment, the period of time between administration of tideglusib or derivative thereof or pharmaceutical formulations thereof and the secondary agent can range from 10 minutes to about 96 hours. In some embodiments the period of time can be about 10 minutes, about 30 minutes, about 1 hour, about 2 hours, about 4 hours, about 6 hours, about 8 hours, about 10 hours, or about 12 hours. The sequential administration can be repeated as necessary over the course of the period of treatment.

The amount of the tideglusib or derivative thereof and pharmaceutical formulations thereof that can be administered are described elsewhere herein. The amount of the secondary agent (also referred to herein as an auxiliary agent or additional agent) will vary depending on the secondary agent. The amount of the secondary agent can be a therapeutically effective amount. In some embodiments, the effective amount of the secondary agent ranges from 0.001 micrograms to about 1 milligram. In other embodiments, the amount of the secondary agent ranges from about 0.01 IU to about 1000 IU. In further embodiments, the amount of the secondary agent ranges from 0.001 mL to about 1 mL. In yet other embodiments, the amount of the secondary agent ranges from about 1% w/w to about 50% w/w of the total pharmaceutical formulation. In additional embodiments, the amount of the secondary agent ranges from about 1% v/v to about 50% v/v of the total pharmaceutical formulation. In still other embodiments, the amount of the secondary agent ranges from about 1% w/v to about 50% w/v of the total secondary agent composition or pharmaceutical formulation.

In some embodiments, the composition or formulation containing tideglusib or derivative thereof is administered to a patient via an injection. Suitable methods of injection include, but are not limited to. intravenous, intraperitoneal, subcutaneous, intramuscular, intradermal, intraosseous, epidural, intracardiac, intraarticular, intracavernous, intrathecal, intravireal, intracerebral, and intracerebroventricular injection Other suitable methods of administration of the composition or formulation containing tideglusib or derivative thereof or pharmaceutical formulation thereof include, but are not limited to, topical, transdermal, nasal, or oral delivery. In some embodiments, the dosage of tideglusib or derivative thereof ranges from about 0.01 µg/g or less bodyweight to about 10 mg/g bodyweight or more.

Kits Containing Tideglusib or Derivative Thereof and Formulations Thereof

The tideglusib and derivatives thereof and pharmaceutical formulations thereof described herein can be presented as a combination kit. As used herein, the terms "combination kit" or "kit of parts" refers to the tideglusib and derivatives thereof and pharmaceutical formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the tideglusib and derivatives thereof and pharmaceutical formulations thereof and/or other auxiliary and/or secondary agent contained therein, safety information regarding the content of the tideglusib and derivatives thereof and pharmaceutical formulations thereof and/or other auxiliary and/or secondary agent contained therein, information regarding the dosages, indications for use, and/or recommended treatment regimen(s) for tideglusib and derivatives thereof and pharmaceutical formulations thereof and/or other auxiliary and/or secondary agent contained therein. In some embodiments, the instructions can provide directions for administering the tideglusib and derivatives thereof and pharmaceutical formulations thereof and/or other auxiliary and/or secondary agent to a subject having a CDKL5 deficiency, Rett syndrome, and/or a symptom thereof.

Age of Intervention

The tideglusib or derivatives thereof and pharmaceutical formulations thereof described herein can be used for the treatment and/or prevention of a disease, disorder, syndrome, or a symptom thereof in a subject, particularly subjects of a certain age group. In some embodiments, tideglusib or derivatives thereof and pharmaceutical formulations thereof can be used to treat and/or prevent a CDKL5 deficiency, Rett syndrome, variants of Rett syndrome, and/or a symptom thereof in a subject that is an infant, child, juvenile, adolescent or young adult.

In various embodiments, the subject to be administered tideglusib or derivatives thereof and pharmaceutical formulations thereof is a certain age, such as less than or equal to 21, 18, 16, 13, 12, 11, 10, 9, 8, 7, 5, 4, 3, 2, 1 years of age or less than or equal to 24, 18, 12, 10, 9, 8, 7, 6, 5, 4, 3, 2 or 1 months of age. As is further provided in the examples below, it is believed that initiating therapy with tideglusib or derivatives thereof and pharmaceutical formulations thereof as described herein at earlier ages will be more beneficial than initiating therapy at later ages. For example, initiating therapy at an age when GSK3β and/or CDKL5 activity is high is expected to be more beneficial than initiating therapy at an age when GSK3β and CDKL5 activity is low.

Without further elaboration, it is believed that one skilled in the art can, based on the description herein, utilize the present disclosure to its fullest extent. It is emphasized that the embodiments of the present disclosure, particularly any "preferred" embodiments, are merely possible examples of the implementations, merely set forth for a clear understanding of the principles of the disclosure. Many variations and modifications may be made to the disclosed embodiment(s) of the disclosure without departing substantially from the spirit and principles of the disclosure. All such modifications and variations are within the scope of this disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Materials and Methods

Colony

Mice for testing were produced by crossing $Cdkl5^{+/-}$ KO females with $Cdkl5^{-/Y}$ KO males and $Cdkl5^{+/-}$ KO females with $Cdkl5^{+/Y}$ KO males. Littermate controls were used for all the experiments. Animals were karyotyped by PCR on genomic DNA using the following primers:

```
108F:  5'-ACGATAGAAATAGAGGATCAACCC-3';

109R:  5' CCCAAGTATACCCCTTTCCA-3';

125R:  5'-CTGTGACTAGGGGCTAGA-3'.
```

The kit used for the PCR was the GO TAQ Flexi DNA Polymerase (Promega). The expected product sizes were 240 bp for the WT mouse and 344 bp for the Cdkl5 KO mice.

Figure 2:
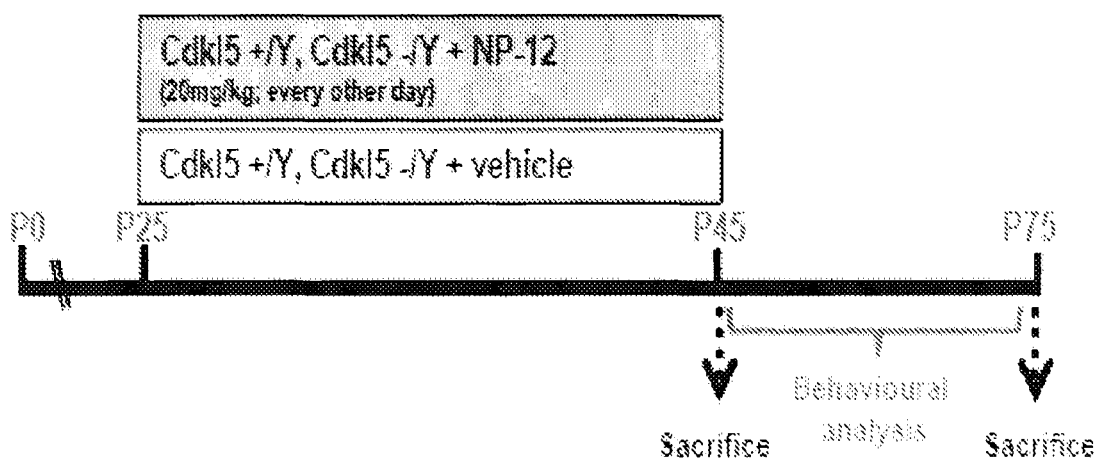
FIG. 2 shows an experimental protocol. Starting from postnatal day 25 (P25), Cdkl5$^{+/Y}$ and Cdkl5$^{-/Y}$ male mice were treated with vehicle or NP-12, administered by subcutaneous injection every other day for 20 days. Animals were sacrificed 4 hours after the last injection (on P45) or after one month (on P75). Some animals from each experimental group were behaviorally tested as indicated. Abbreviations: P, postnatal day.

The day of birth was designed as postnatal day (P) zero (P0) and animals with 24 hours of age were considered as one-day-old animals (P1). After weaning, mice were housed three to five per cage and were on a 12-hour (h) light/dark cycle in a temperature-controlled environment with food and water provided ad libitum. Starting from postnatal day 25 (P25), Cdkl5$^{+/Y}$ WT and Cdkl5$^{-/Y}$ KO male mice were treated with vehicle (corn oil; Sigma-Aldrich) or NP-12 (20 mg/kg; Sigma-Aldrich), administered by subcutaneous injection every other day for 20 days. Animals were sacrificed 4 hours after the last injection on P45. Some animals from each experimental group were behaviorally tested after the last injection as shown in FIG. 2.

Primary Hippocampal Culture

Hippocampal neurons were prepared from postnatal day 1 (P1) Cdkl5$^{-/Y}$ and Cdkl5$^{X/Y}$ male mice. Briefly, hippocampi were dissected from mouse brains under a dissection microscope and treated with trypsin (Sigma Aldrich) for 15 min at 37° C. and DNase (Sigma Aldrich) for 2 min at room temperature before triturating mechanically with fire-polished glass pipette to obtain a single-cell suspension. Approximately 1.2×10$^5$ cells were plated on coverslips coated with poly-1-lysine in 12-well plates and cultures in Neurobasal medium (Invitrogen) supplemented with B27 (Invitrogen) and glutamine (Invitrogen). Cells were maintained in vitro at 37° C. in a 5% $CO_2$-humified incubator and fixed for immunostaining or Western Blot analysis at 10 days after plating (DIV10). 1 µM NP-12 (Sigma) was administrated on alternate days.

Western Blot Analysis

For Western Blot analysis hippocampal neurons at DIV10 were lysed in ice-cold RIPA lysis buffer (50 mM Tris-HCl pH 7.4, 150 mM NaCl, 1% Triton-X100, 0.5% sodium deoxycholate, 0.1% SDS) supplemented with 1 mM PMSF and 1% proteases and phosphatases inhibitor cocktail (Sigma). Cell extracts were immediately processed by Western blot or kept frozen (−80° C.) until assayed. The whole protein cell extract were subjected to electrophoresis on a 4-12% Mini-PROTEAN® TGX™ Gel (Bio-Rad) and transferred to a Hybond ECL nitrocellulose membrane (Amersham Life Science). The following primary antibodies were used: anti-phospho-GSK3-β-Ser9 (1:1000; Cell Signaling Technology), anti-GSK3-β (1:1000; Cell Signaling Technology) and anti-MAP2 (1:1000, Millipore). Densitometric analysis of digitized images was performed with Scion Image software (Scion Corporation, Frederick, Md., USA) and intensity for each band was normalized to the intensity of the respective GSK3β levels (normalized to the neuronal protein levels MAP-2).

Immunocytochemistry

Immunostaining for cultured hippocampal neurons were performed with the following procedure. Cells were fixed in 4% PFA+4% sucrose in PBS for 20 min and washed five times in PBS. After permeabilization with PBST cells were incubated overnight at 4° C. o/n with the following antibodies: rabbit polyclonal anti-MAP2 (1:100, Millipore) and SYN (SY38) antibody (1:1000, MAB 5258, Merck Millipore). Sections were then incubated for 2 h at room temperature with a FITC-conjugated goat anti-mouse IgG (1:100; Sigma-Aldrich) and a Cy3-conjugated anti-rabbit IgG (1:100, Jackson Immunoresearch).

Fluorescent images were taken with an Eclipse TE 2000-S microscope (Nikon, Tokyo, Japan) equipped with an Axio-Cam MRm (Zeiss, Oberkochen, Germany) digital camera.

Polarization Analyses

Figure 3:
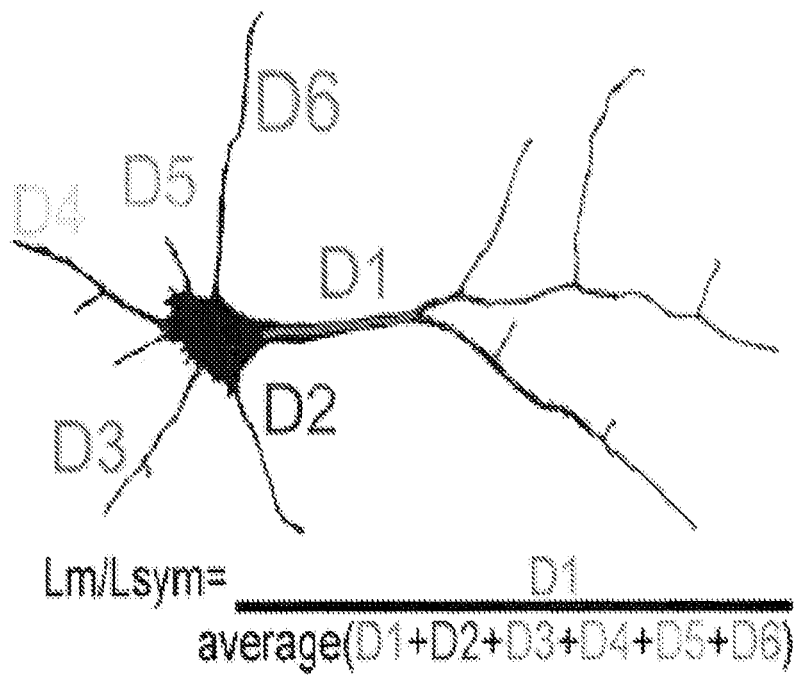
FIG. 3 demonstrates the polarization assessment. The length of the longest dendrite/axon D1 (Lm) is divided by the average length of all dendrites D1, D2, D3, D(n) (Lsym). The dendritic arbour is polarized when the apical dendrite is specified, i.e., when Lm/Lsym=2. Figure is adapted from Baj et al. 2014. Front. Cell Neurosci. 8:18.

To define the degree of polarization of neuronal dendrites, we followed the method described by Horton et al. (FIG. 3) (Horton et al. 2006. Brain Cell. Biol. 35:29-38). Briefly, the measured lengths of dendrites (Lm) in each neuron (including the primary dendrite/axon with all its branches) were ranked highest to lowest. The sum of these length is the total dendritic length for that neuron (Lsym). If neurons were symmetric (i.e., with dendrites of similar lengths), that value would be Lm=Lsym=1/number of dendrites (Lm/Lsym=1). If neurons were asymmetric (i.e., with dendrites of different lengths), the ratio Lm/Lsym would reflect the degree to with dendrites diver from perfect symmetry. All neurons that showed an Lm/Lsym value above threshold 2 were considered as polarized neurons.

Morphological Analysis

The morphological analysis of hippocampal neurons was focused on two parameters: length of the longest dendrite (D1) and total dendritic length. To achieve this aim, dendritic length of MAP2-positive neurons were measured and quantified by tracing along each neuronal projection using the image analysis system Image Pro Plus (Media Cybernetics, Silver Spring, Md. 20910, USA). The starting point of a dendrite was defined as the point at the midline of the dendrite that intersected the curvature of the soma. For our measures, protrusions emerging from the cell soma with all its branches were counted as a single dendrite, tracing the entire dendritic arbor.

Histological Procedures

Some animals were deeply anesthetized with ether on P45, and the brain was removed and fixed by immersion in 4% paraformaldehyde (PFA) in 100 mM phosphate buffer, pH 7.4. Brains were stored in the fixative for 24 h, cut along the midline and kept in 20% sucrose in phosphate buffer saline (PBS) for an additional 24 h. Hemispheres were frozen and stored at −80° C. The right hemisphere was cut with a freezing microtome into 30-µm-thick coronal sections that were serially collected in antifreeze solution containing glycerol, ethilene glycol, PBS 10×, bidistillate water and sodium azide.

Immunohistochemistry

One out of 6 sections from the hippocampal formation were used for immunohistochemistry for cleaved caspase-3 (1:200, anti-cleaved caspase-3 rabbit polyclonal Ab, Cell Signaling Technology), doublecortin (1:100, anti-DCX goat polyclonal Ab, Santa Cruz Biotechnology), synaptophysin (1:1000, anti-SYN (SY38) mouse monoclonal Ab, MAB 5258, Merck Millipore) and PSD-95 (1:1000, anti-PSD-95 rabbit polyclonal Ab, Abcam) or double fluorescence immunohistochemistry for synaptophysin, and PSD-95.

For cleaved caspase-3, the section were incubated o/n at 4° C. with a rabbit antibody (1:200, anti-cleaved caspase-3 rabbit polyclonal Ab, Cell Signaling Technology) and for 2 h at room temperature with a HRP-conjugated anti-rabbit secondary antibody (1:200, Jackson Immunoresearch). Detection was performed using TSA Cyanine 3 Plus Evaluation Kit (Perkin Elmer).

For DCX immunohistochemistry, sections from the DG were incubated o/n at 4° C. with a goat polyclonal anti-DCX antibody (1:100, Santa Cruz Biotechnology). Sections were then incubated for 2 h at room temperature with a biotinylated anti-goat IgG secondary antibody (1:200, Vector Laboratories) and thereafter incubated for 1 h with VECTASTAIN® ABC kit (Vector Laboratories). Detection was performed using DAB kit (Vector Laboratories). In this type of immunohistochemistry bright field images were taken with a Leitz Diaplan microscope equipped with a motorized stage and a Coolsnap-Pro digital camera (Media Cybernetics, Silver Spring, Md., USA).

For synaptophysin immunohistochemistry, sections were incubated o/n at 4° C. with a mouse monoclonal anti-SYN (SY38) antibody (1:1000, MAB 5258, Merck Millipore) and for 2 h at room temperature with a FITC-conjugated goat anti-mouse IgG secondary antibody (1:200; Jackson Immunoresearch).

For PSD-95 immunohistochemistry, sections from the DG were incubated o/n at 4° C. with an anti-PSD-95 antibody (1:1000, rabbit polyclonal antibody, Abcam) and for 2 h at room temperature with a Cy3-conjugated anti-rabbit IgG secondary antibody (1:200, Jackson Immunoresearch).

For double-fluorescence immunostaining, sections were incubated o/n at 4° C. with a primary antibodies SYN (SY38) antibody (1:1000, MAB 5258, Merck Millipore) and PSD-95 (1:1000, rabbit polyclonal antibody, Abcam). Sections were then incubated for 2 h at room temperature with a FITC-conjugated goat anti-mouse IgG (1:100; Sigma-Aldrich) for SYN immunohistochemistry and a Cy3-conjugated anti-rabbit IgG (1:100, Jackson Immunoresearch) secondary fluorescent antibody for PSD-95 immunohistochemistry.

Golgi Staining

Brains were Golgi-stained using the FD Rapid Golgi Stain™ Kit (FD NeuroTechnologies, Inc., Columbia, Md., USA). The brains were immersed in the impregnation solution, made by mixing equal volumes of Solutions A and B, and store at room temperature for 2 weeks in the dark. Then, the tissue was transferred into Solution C and stored at room temperature in the dark for at least 72 hours. Finally, sections of the tissue were cut with a freezing microtome into 90-µm-thick coronal sections with a cryostat at −40° C. to −43° C.

Cell Counting

The total number of positive cells in the DG (cleaved caspase-3, DCX) was estimated by multiplying the total number counted in the series of sampled sections by the inverse of the section sampling fraction (ssf=⅙). The total number of cells of each phenotype was estimated by multiplying the number counted in the series of sections by the inverse of the section sampling fraction (ssf=⅙).

Measurement of the Dendritic Tree

Figure 4:
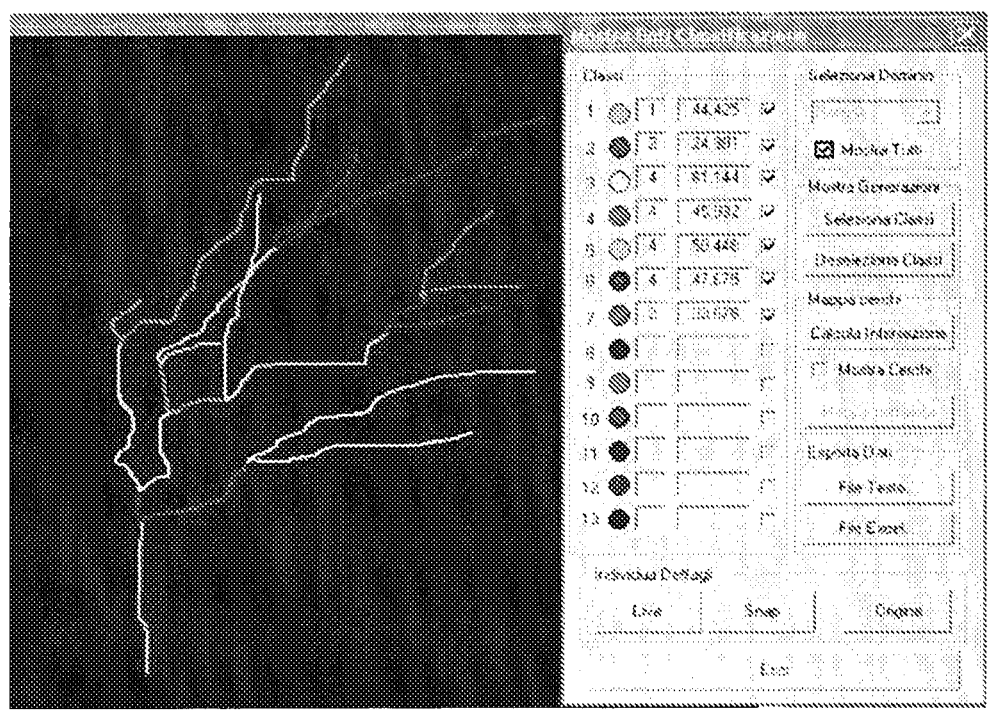
FIG. 4 demonstrates an example of a dendritic trace. Image was reconstructed by Image Pro Plus (Media Cybernetics, Silver Spring, Md. 20910, USA) at the end of the tracing.
Figure 5:
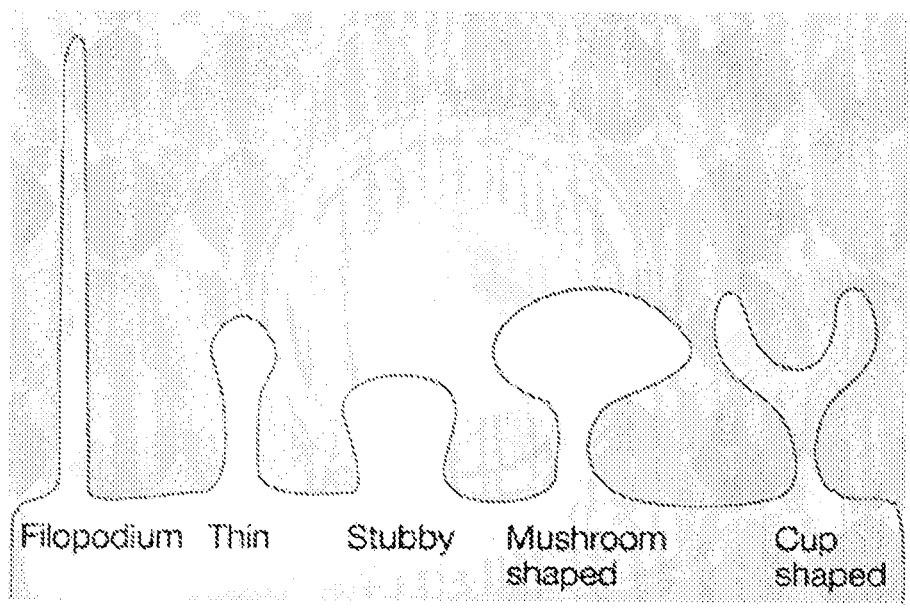
FIG. 5 shows a cartoon depicting the morphological classification of dendritic spines. Image adapted from Hering and Sheng. 2001. Nat. rev. Neurosci. 2:880-888.

Dendritic trees of DCX-positive granule cells sampled in the inner part of the granule cell layer, close to the subgranular zone, and Golgi-stained granule cells and CA1 pyramidal neurons were traced with dedicated software, custom-designed for dendritic reconstruction (Immagini Computer, Milan, Italy), interfaced with Image Pro Plus (Media Cybernetics, Silver Spring, Md. 20910, USA). The dendritic tree was traced live, at a final magnification of 100×, by focusing into the depth of the section. The operator starts with branches emerging from the cell soma and after having drawn the first parent branch goes on with all daughter branches of the next order. At the end of tracing the program reconstructs the trace (FIG. 4), the number and length of individual branches, the mean length of branches of each order and total dendritic length.

Synaptic Density in the Molecular Layer of the DG

The connectivity in the molecular layer of the dentate gyrus (DG) was evaluated using double SYN and PSD-95 immunohistochemistry as previously described. To evaluate the connectivity in the molecular layer of the DG, intensity of SYN and PSD-95 immunoreactivity (IR) was determined by optical densitometry of immunohistochemically stained sections. Fluorescence images were captured using an Eclipse TE 2000-S microscope (Nikon, Tokyo, Japan) equipped with an AxioCam MRm (Zeiss, Oberkochen, Germany) digital camera. Densitometric analysis of SYN and PSD-95 in the inner (I), middle (M) and outer (0) third of the molecular layer was carried out using Nis-Elements Software 3.21.03 (Nikon). For each image, the intensity threshold was estimated by analyzing the distribution of pixel intensities in the image areas that did not contain IR. This value was then subtracted to calculate the IR of each sampled area. The optical density (OD) was evaluated in a box of 1600 µm$^2$ randomly placed at five different sites in the molecular layer of the upper blade of the DG. The OD of the sampled regions was corrected by the background.

Synaptic Density (Puncta) in the Molecular Layer of the DG Acquired with Con Focal Microscope.

A box of 36 µm$^2$ was placed in the inner and middle part of the molecular layer of the dentate gyrus. Images immunoprocessed for SYN or PSD-95 were acquired with a confocal microscope at 63× objective Leica TCS confocal microscope (Leica Microsystems, Wetzlar, Germany). In each section two images from the inner and middle portion of the molecular layer were captured and the density of individual puncta exhibiting SYN or PSD-95 immunoreactivity was evaluated by counting all the puncta in the box.

Spine Density/Morphology

Figures 17A, 17B, 17C:
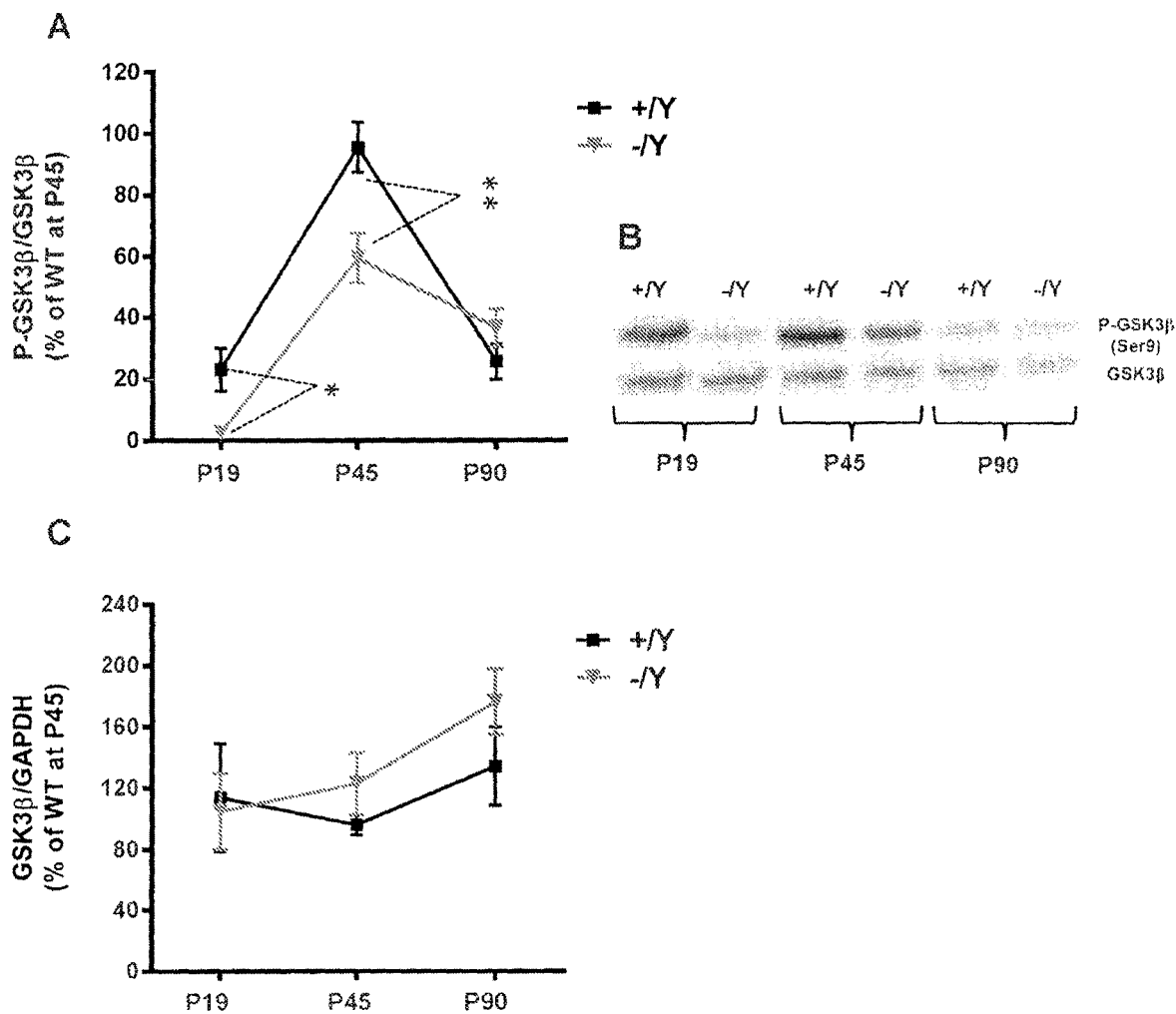
FIGS. 17A-17C show graphs demonstrating the results from Western Blot analysis of P-GSK3β-Ser9 (A,B) and GSK3β (C) levels in the hippocampal formation of wildtype (+/Y) and Cdkl5 (−/Y) male mice at different ages (P19 (+/Y n=4, −/Y n=4), P45 (+/Y n=9, −/Y n=9), P90 (+/Y n=4, −/Y n=4)). Western immunoblot in B is an example from one animal of each experimental group. Histograms in A and C show P-GSK3β-Ser9 levels normalized to total GSK3β levels (A) and GSK3β levels normalized to glyceraldehyde-3-phosphate dehydrogenase (GAPDH) levels (C). Data are expressed as fold difference in comparison to Cdkl5+/Y mice aged P45. Values are represented as means±SD. $*p<0.05$; $**p<0.01$ as compared to the corresponding Cdkl5+/Y condition; (Duncan's test after ANOVA).

In Golgi-stained sections, spines of granule cells were counted using a 100× oil immersion objective lens. Dendritic spine density was measured by manually counting the number of dendritic spines on dendritic segments in the inner and outer half of the molecular layer and expressed as the number of dendritic spines per 20 µm dendritic length. The dendritic spine length was measured by manually drawing a vertical line from the tip of the protrusion to the point where it met the dendritic shaft. The number of spine clusters was counted manually on dendritic segments in the inner and outer half of the molecular layer and expressed as number of spine clusters per 20 µm dendritic length. The dendritic spines density was divided between the different type of shapes morphology, expressed in percentage. In fact, dendritic spines can have different shapes morphology based on their maturation (FIG. 17). The number of spines belonging to the different group was counted.

Western Blotting

The brain of some animals from experimental group was quickly removed and the hippocampal formation was dissected, kept at −80° C. and total proteins were extracted and processed for Western blotting. For the preparation of hippocampal extracts, tissues were homogenized in RIPA buffer (Tris-HCl, 50 mM, NaCl 150 mM, Triton X-100 1%, SDS, 0.1%, sodium deoxycholate 0.5%, PMSF 1 mM, 1 mM PMSF protease and phosphatase inhibitors cocktails 1% (Sigma)). Extracts were immediately processed by Western blot or kept frozen (−80° C.) until assayed. Sample protein concentration was estimated by the Lowry method. Equivalent amounts (50 µg) of protein were subjected to electrophoresis on a 10% SDS-polyacrylamide gel (Mini-PROTEAN® TGX™ Gel (Bio-Rad)), transferred to a Hybond ECL nitrocellulose membrane (Amersham Life Science) and incubated with the following antibodies: anti-GAPDH (glyceraldehyde-3-phosphate dehydrogenase) (1:5000, rabbit polyclonal, Sigma-Aldrich); anti-phospho-GSK3β-Ser9 (P-GSK3β-Ser9) (1:1000, mouse mAb, Cell Signaling Technology), anti-GSK3β (1:1000, mouse mAb, Cell Signaling Technology) and anti β-catenin (1:1000; BD Transduction Laboratories), overnight at 4° C. Densitometric analysis of digitized images with ChemiDoc XRS+ was performed with Scion Image software (Scion Corporation, Frederick, Md., USA). The intensity for each band was normalized: P-GSK3β-Ser9 levels was normalized to total GSK3β levels and β-catenin levels was normalized to GAPDH levels.

Behavioural Testing

Passive Avoidance (PA).

For the PA test we used a tilting-floor box (47×18×26 cm) divided into two compartments by a sliding door and a control unit incorporating a shocker (Ugo Basile, Italy). This classic instrument for Pavlovian conditioning exploits the tendency in mice to escape from an illuminated area into a dark one (step-through method). On the first day mice were individually placed into the illuminated compartment. After 60 seconds of habituation period, the connecting door between the chambers opened. In general, mice step quickly through the gate and enter the dark compartment because mice prefer to be in the dark. Upon entering the dark compartment, mice received a brief foot shock (0.7 mA for 3 seconds) and were removed from the chamber after 15 seconds of latency. If the mouse remained in the light compartment for the duration of the trial (358 s), the door closed and the mouse was removed from the light compartment. The chambers were cleaned with 70% ethanol between testing of individual mice. After a 24 hour retention period, mice were placed back into the light compartment and the time it took them to re-enter the dark compartment (latency) was measured up to 358 seconds.

Statistical Analysis

Data from single animals represented the unity of analysis. Results are presented as mean standard error of the mean (±SE). Statistical testing was performed using a two-way analysis of variance (ANOVA) with genotype (Cdkl5$^{+/Y}$; Cdkl5$^{-/Y}$) and treatment (vehicle or NP-12) as fixed factors and mouse as random factor, or using a one-way ANOVA followed by Fisher LSD post hoc test or Duncan's test. A probability level of P<0.05 was considered to be statistically significant.

Results

Effect of Tideglusib (NP-12) Treatment on Hippocampal Neurons from CDKL5 Knockout Mice GSK3β regulates several neurodevelopmental processes, including neuronal maturation and dendritic development. Recently, it was observed that disruption of the AKT/GSK3β signaling pathway with increased GSK3β activity in neural precursor cells of Cdkl5 KO mice. In order to establish the effects of GSK3β inhibition on neuronal maturation, the effects of chronic NP-12 treatment on hippocampal neuronal cultures of Cdkl5 KO mice were investigated. GSK3β activity is inhibited by phosphorylation at Ser9. By Western blot analysis, it was observed that primary neurons from Cdkl5 KO mice show significantly reduced phosphorylation levels of GSK3β at Ser9 (FIGS. 6 A,B), confirming that loss of CDKL5 affect GSK3β activity also in Cdkl5 KO hippocampal cultures. Chronic treatment with NP-12 (1 μm) starting from DIV2 completely restores GSK3β Ser9-phosphorylation in hippocampal cultures of Cdkl5" mice (FIGS. 6 A,B).

Figures 6A, 6B, 6C, 6D, 6E:
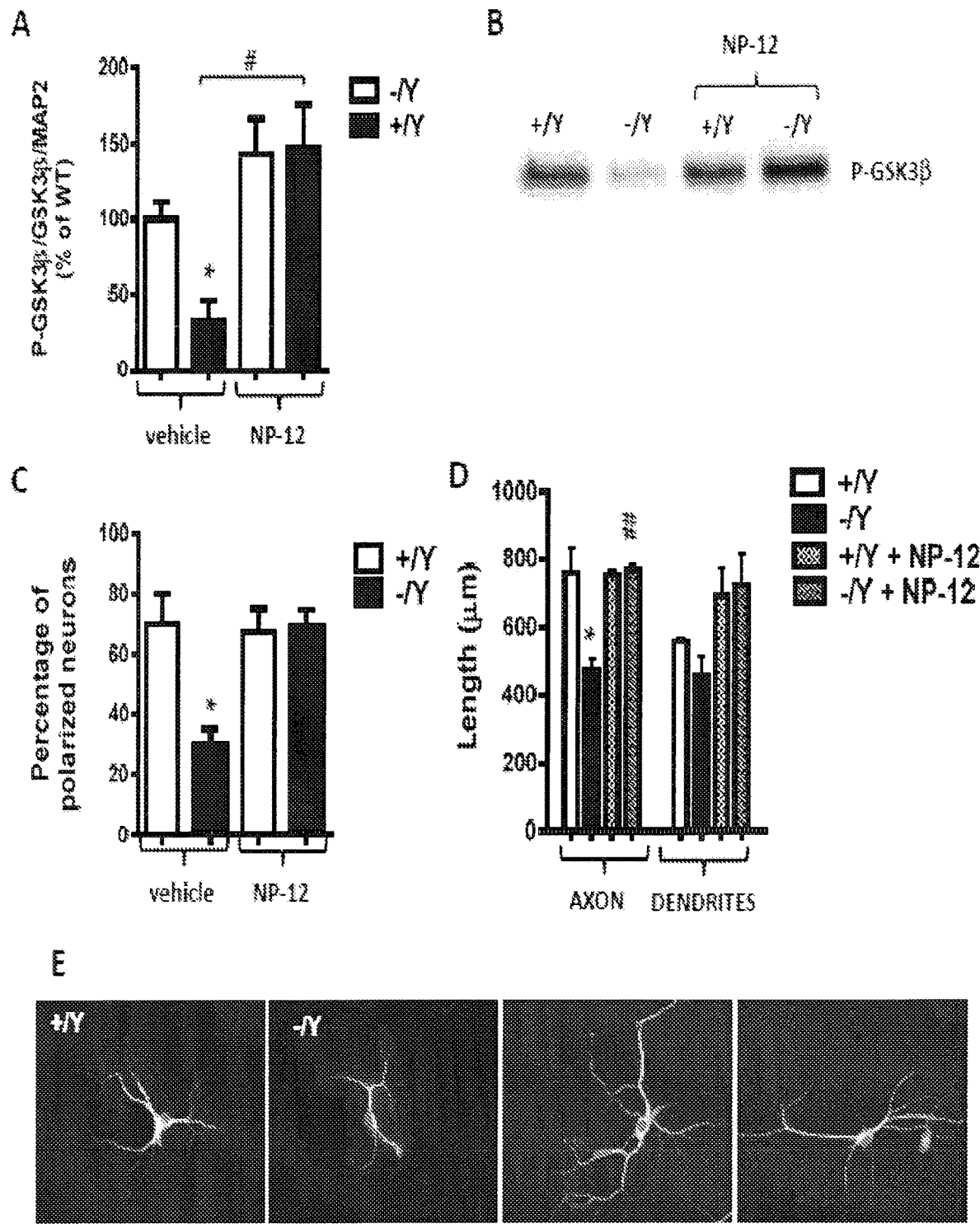
FIGS. 6A-E demonstrate results from western blot analysis of P-GSK3β-Ser9 levels in hippocampal neurons from WT (+/Y) and Cdkl5 KO (−/Y) male mice (DIV10). Hippocampal cultures were treated with 1 µm NP-12 starting from DIV2. The immunoblot in B is an example from one animal of each experimental group. The histogram in A shows P-GSK3β-Ser9 levels normalized to total GSK3β levels normalized to the number of neurons in culture (expressing MAP2). (C-D) Graphs showing the percentage of polarized neurons (C) and the quantification of the length of the longest axon and dendrite (D) in treated and untreated in hippocampal cultures as in A. (E) Representative images of MAP2-stained hippocampal neurons as in A. Data are expressed as fold difference in comparison to hippocampal neurons from untreated Cdkl5$^{+/Y}$ mice. Values are represented as means±SD. *p<0.05 as compared to the untreated Cdkl5$^{+/Y}$ condition; #p<0.05; ##p<0.01 as compared to the untreated Cdkl5$^{-/Y}$ samples (Duncan's test after ANOVA).

It was next established whether hippocampal primary neurons from Cdkl5 KO mice, show similar developmental defects as those observed in neuronal precursor cells both in vitro and in vivo. It was observed that a loss of Cdkl5 induces a significant decrease in polarized neurons at DIV10 (FIGS. 6 C,E). In addition axonal and dendrite elongation is also impaired in hippocampal cultures from Cdkl5 mutant mice, suggesting that CDKL5 is involved in proper axon specification and elongation and dendrite maturation (FIGS. 6 D,E). As shown in FIGS. 6C and D, inhibition of GSK3β efficiently ameliorated the percentage of polarized neurons (FIG. 6 C) and had positive effects on correct axon and dendrite maturation (FIG. 6 D). Taken together these results suggest that the aberrant polarization phenotype in Cdkl5 KO hippocampal neurons is mediated by GSK3β hyperactivity. Further, the data suggests that reinstatement of GSK3β activity by NP-12 can completely restore these neurodevelopmental defects.

Figure 15:
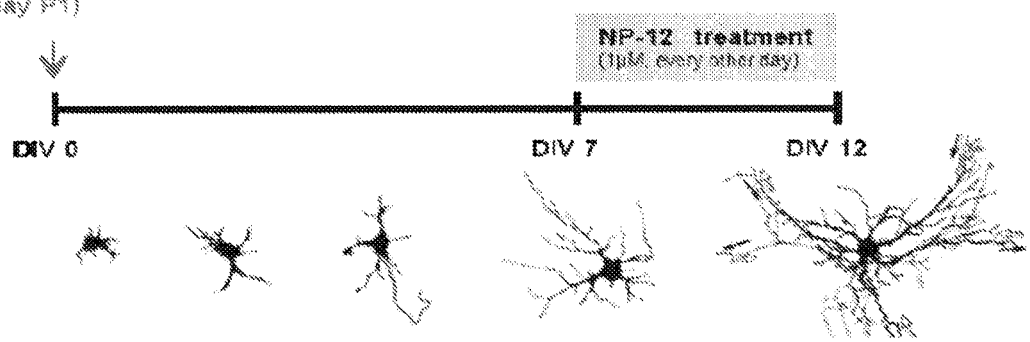
FIG. 15 shows the experimental protocol for an in vitro experiment using cultured hippocampal neuronal cells from CDKL5 KO and wild-type mice.
Figures 16A, 16B:
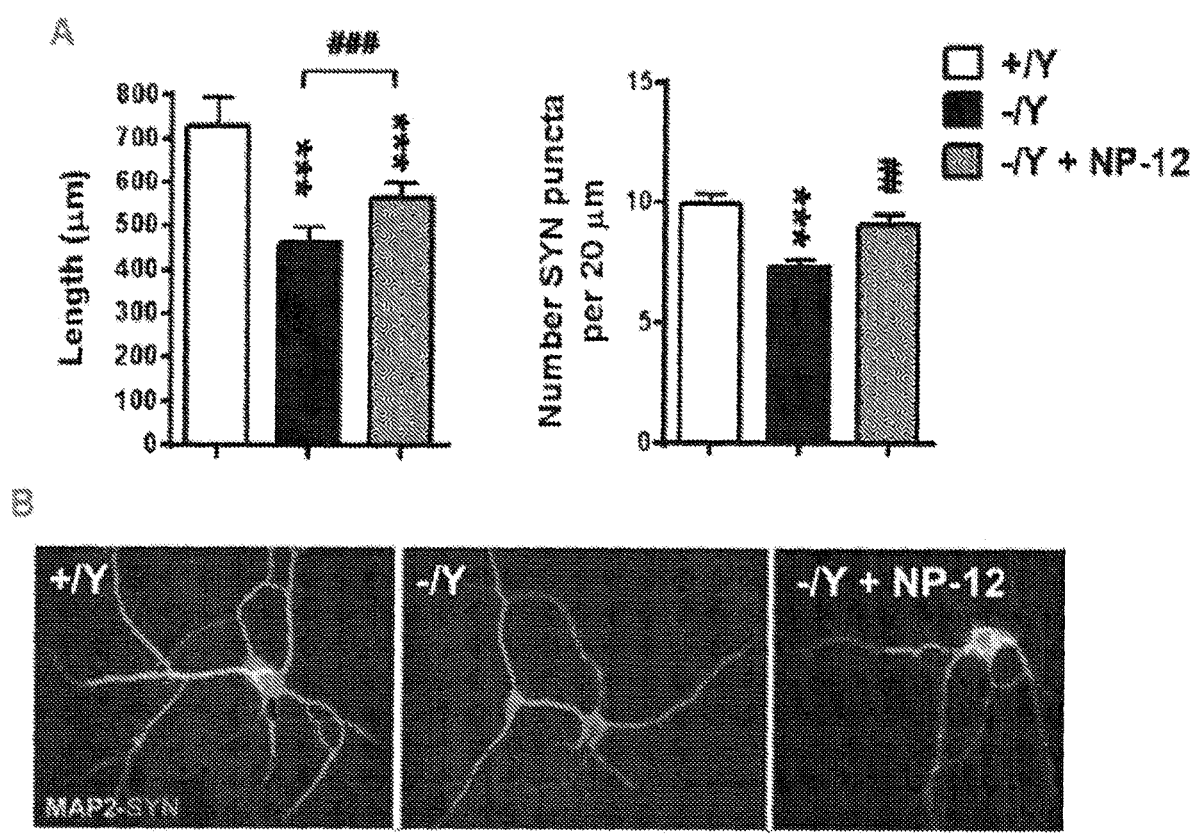
FIGS. 16A-16B shows the number of synaptic puncta of hippocampal neurons from untreated wild-type (+/Y) and Cdkl5 KO (−/Y) male mice (I would exclude graph on the left because it is a repetition). (B) show representative images of immunofluorescence staining for MAP2 (green) and synaptophysin (SYN, red) of hippocampal neuronal cultures from mice as in (A).

In vitro experiments were conducted to evaluate the effect of tideglusib (NP-12) on hippocampal neuronal cultures developed from Cdkl5+/Y, Cdkl5 –/Y mice. To develop the cultures the hippocampal neuronal cells were harvested on postnatal day 1, which was considered division 0 (DIV 0) and cultured in vitro for the remainder of the experiment. NP-12 treatment began at division 7 (DIV7) and was continued until Division 12 (DIV12). The experimental protocol is demonstrated in FIG. 15. NP-12 treatment began on D7. NP-12 was added every other day to the cultures at final concentration of 1 μM. Results are presented as mean±SD. Data were analyzed with Duncan's test after ANOVA. A probability level of p<0.05 was considered to be statistically significant. *P, 0.05, P<0.01, *p<0.001 as compared to the untreated wild-type (Cdkl5+/Y) condition; #p<0.05, ##p<0.01 ###p<0.001 as compared to the untreated Cdkl5 KO (–/Y) samples. The morphological dendritic alterations in Cdkl5 KO ippocampal neurons were associated with a reduction in the number of synaptophysin (SYN) puncta in these neurons (FIG. 16A-B) Number of Syn puncta in Cdkl5 KO ippocampal neurons was completely restore by treatment with NP-12 (FIGS. 16 A-B).

Effect of Tideglusib (NP-12) Treatment on GSK3β Activity In Vivo

Figures 7A, 7B, 7C:
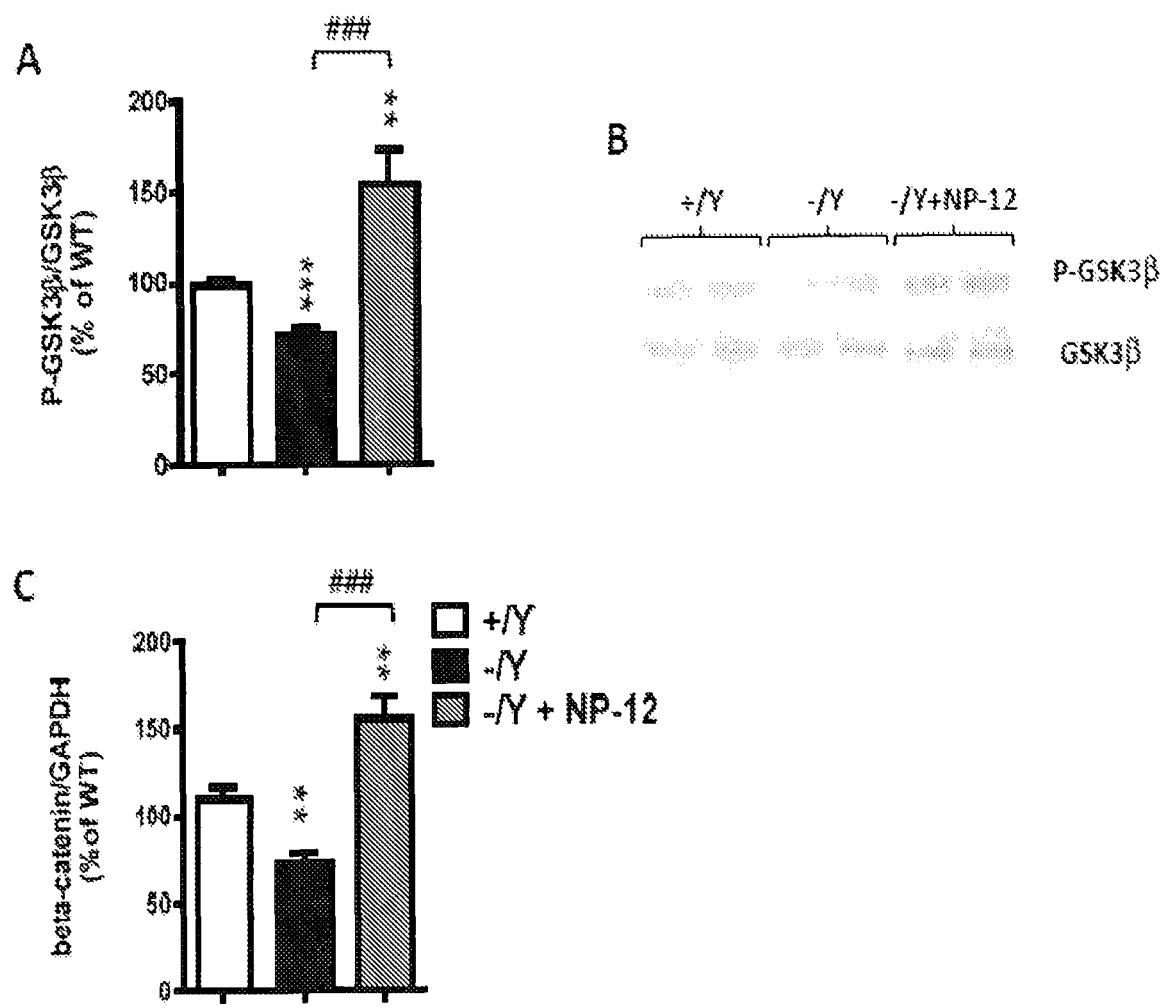
FIGS. 7A-7C demonstrate results from western blot analysis of P-GSK3β-Ser9 (A,B) and β-catenin (C) levels in the hippocampal formation of untreated (+/Y n=4, −/Y n=4) and treated (−/Y n=3) Cdkl5 male mice aged P45. Western immunoblot in B is an example from two animals of each experimental group. Histograms in A and C show P-GSK3β-Ser9 levels normalized to total GSK3β levels (A) and β-catenin levels normalized to glyceraldehyde-3-phosphate dehydrogenase (GAPDH) levels (C). Data are expressed as fold difference in comparison to untreated Cdkl5$^{+/Y}$ mice. Values are represented as means±SD. p<0.01; *p<0.001 as compared to the untreated Cdkl5$^{+/Y}$ condition; ## #p<0.001 as compared to the untreated Cdkl5$^{-/Y}$ samples (Duncan's test after ANOVA).

Juvenile wild type (Cdkl5$^{+/Y}$ and Cdkl5$^{-/Y}$ male mice were treated with the GSK3β inhibitor NP-12 or vehicle for 25 days (see FIG. 2). In order to evaluate the effects of NP-12 treatment on the phosphorylation status of GSK3β Ser9, a Western blot analysis was performed on hippocampal extracts of NP-12 treated Cdkl5 KO male mice. Phosphorylation of GSK3β at Ser9 was reduced in the hippocampus of Cdkl5$^{-/Y}$ mice compared to their WT littermates (Cdkl5$^{+/Y}$) (FIGS. 7 A,B). As expected NP-12 treatment increased Ser9-phosphorylated GSK3β levels in Cdkl5$^{-/Y}$ mice that became even higher to those of the untreated Cdkl5$^{+/Y}$ counterparts (FIGS. 7 A,B). NP-12 treatment had no effect on total GSK3β levels (FIG. 7B, data not shown). It is well known that GSK3β regulates a wide spectrum of neurodevelopmental events through a broad range of substrates. Among these targets GSK3β controls the amount of β-catenin by negatively regulating β-catenin protein stability. In line with the NP-12-induced restoration of the GSK3β phosphorylation, a complete recovery of β-catenin levels in Cdkl5$^{-/Y}$ mice (FIG. 7C) was observed.

Effect of Tideglusib (NP-12) Treatment on Neuronal Survival

Figure 20:
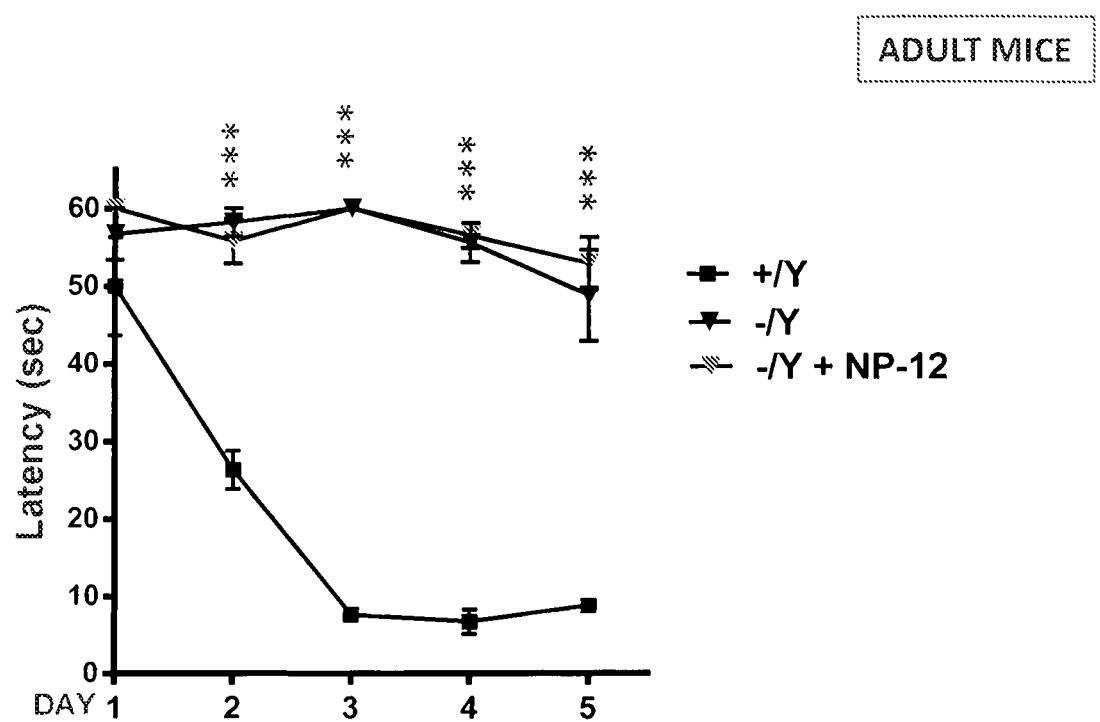
FIG. 20 shows a graph demonstrating results from spatial learning assessed with the Morris water maze in untreated (+/Y n=5, −/Y n=4) and treated (−/Y n=5) Cdkl5 male mice aged P90 at the end of treatment. Values represent mean±SE. $*p<0.05$, $***p<0.001$ as compared to the untreated Cdkl5+/Y condition; $\#\#p<0.01$ as compared to the untreated Cdkl5 −/Y condition. (Duncan's test after ANOVA).

Survival of postmitotic neurons is severely impaired in Cdkl5$^{-/Y}$ mice. Cdkl5 mutant mice show higher proliferation rate of neural precursor cells paralleled by an increase in apoptotic cell dea. In order to evaluate the efficacy of NP-12 treatment on neuronal survival, the number of apoptotic cells expressing cleaved caspase-3 in the dentate gyrus of treated Cdkl5$^{-/Y}$ mice was counted. It was observed that the increased cell death in Cdkl5 KO male mice was completely restored by NP-12 treatment (FIG. 20A), suggesting that restoration of GSK3β signaling has a positive impact on cell survival in Cdkl5 KO mice.

Figures 8A, 8B, 8C:
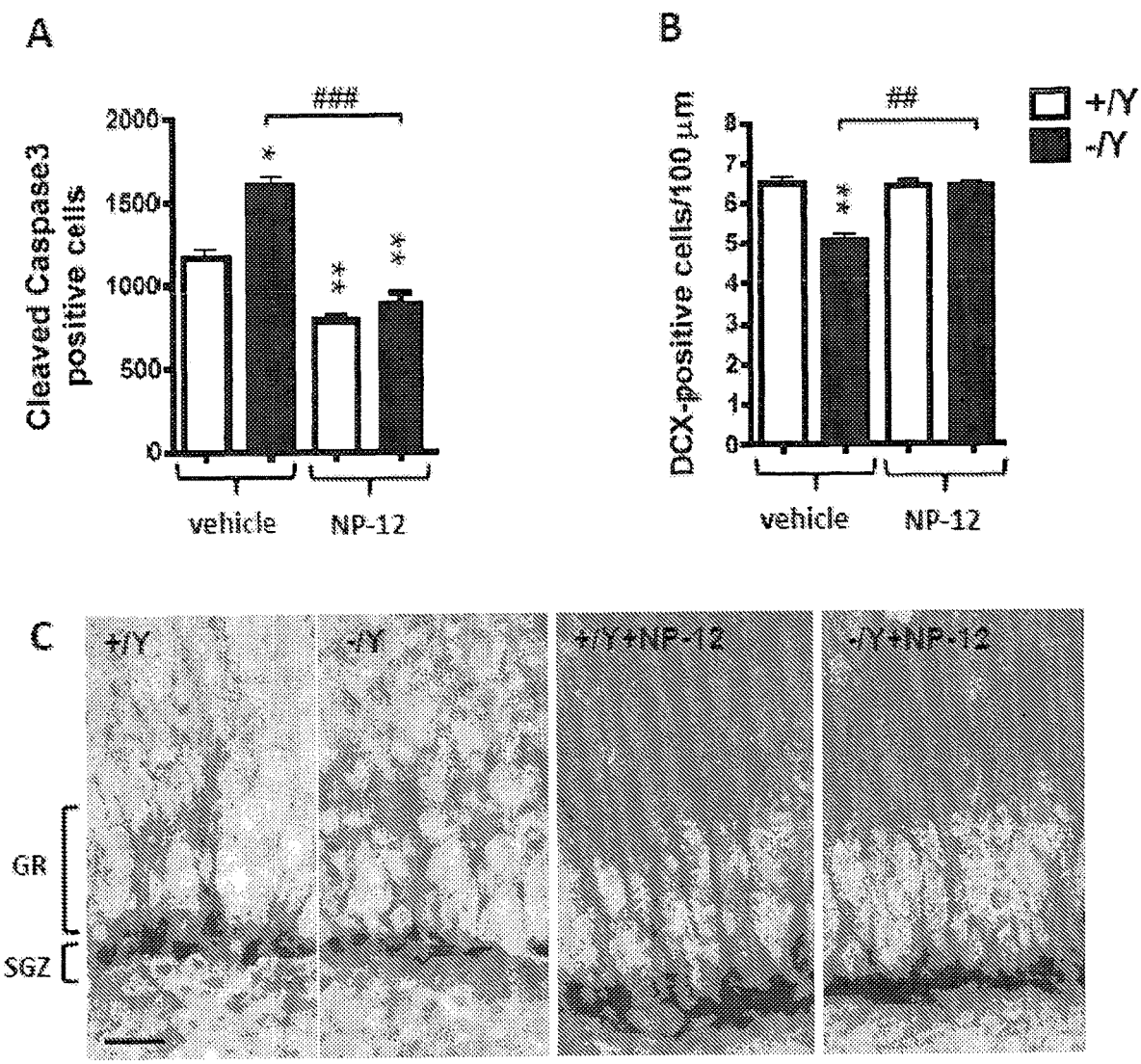
FIGS. 8A-8C demonstrate the (A) Number of cleaved caspase-3 positive cells in the dentate gyrus (DG) of untreated (+/Y n=3, −/Y n=3) and treated (+/Y n=3, −/Y n=3) Cdkl5 male mice. (B,C) Examples of sections processed for DCX immunostaining from the dentate gyrus (DG) of untreated and treated Cdkl5$^{+/Y}$ and Cdkl5$^{-/Y}$ male mice. (C). The photomicrograph shows examples of immature DCX-positive neurons (vertical orientation with long apical processes; red asterisks) in the innermost portion of the granule cell layer (GR) and type 2b/3 DCX-positive precursor cells (orientation parallel to the GR) in the subgranular zone (SGZ). Scale bar=30 µm; type 2b/3 cells and immature neurons were counted separately. (B) Number of DCX-positive type 2b/3 precursor cells and DCX-positive immature neurons in the DG of mice of untreated (+/Y n=3, −/Y n=3) and treated (+/Y n=3, −/Y n=3) Cdkl5 mice. Values in A represent totals for one DG (mean±SD), data in B are expressed as number of cells/100 µm. *p<0.05; **p<0.01 as compared to the untreated Cdkl5$^{+/Y}$ condition; ##p<0.01; ###p<0.001 as compared to the untreated Cdkl5$^{-/Y}$ samples (Duncan's test after ANOVA). Abbreviations: GR, granular layer; SGZ, subgranular zone.

In the course of postnatal hippocampal neurogenesis, new cells within the subgranular zone (SGZ) of the dentate gyrus (DG) go through a series of stages associated with proliferative activity, from the stem cell stage (type 1) to the intermediate progenitor stages (type 2/3), and onto postmitotic maturation. DCX is a protein expressed by type 2b and type 3 intermediate progenitor cells (FIG. 8C), as well as by immature granule neurons (FIG. 8C: red asterisks). Since these cell types have a different orientation (immature neurons show a vertical orientation with long apical processes), it is possible to count them separately. Cdkl5 loss-of-function specifically affects the survival of immature DCX-positive neurons. In order to establish whether NP-12 treatment restores the survival rate of newborn neurons, the number of DCX-positive immature neurons in the dentate gyrus of treated and untreated mice was evaluated. We found that treated $Cdkl5^{+/Y}$ mice underwent an increase in the number of DCX-positive neurons, that became similar to that of untreated $Cdkl5^{+/Y}$ littermates (FIGS. 20B,C).

Taken together the results indicate that treatment with NP-12 restores the survival rate of the postmitotic granule cells in $Cdkl5^{-/Y}$ mice.

Figures 9A, 9B, 9C:
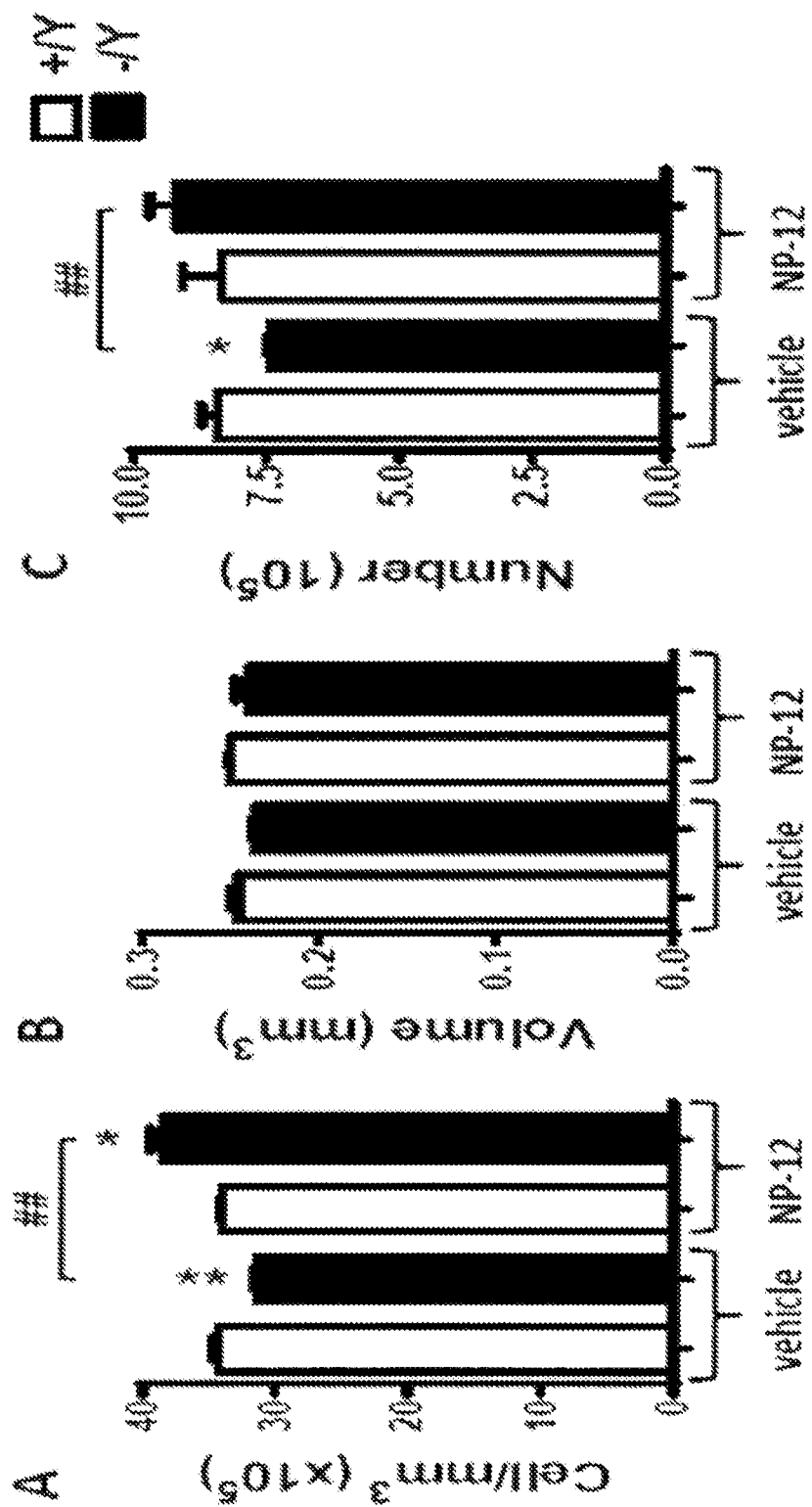
FIGS. 9A-9C demonstrate (A,C) the density of granule cells (A), volume of the granule cell layer (B), and total number of granule cells (C) in the dentate gyrus (DG) of untreated (+/Y n=4, −/Y n=4) and treated (+/Y n=3, −/Y n=3) Cdkl5 male mice aged P45. Values in A-C refer to one DG (mean±SD). $*p<0.05$; $**p<0.01$ as compared to the untreated $Cdkl5^{+/Y}$ condition; $\#\#p<0.01$ as compared to the untreated $Cdkl5^{-/Y}$ samples (Duncan's test after ANOVA).

Effect of Tideglusib (NP-12) on Net Number of Granule Cells in the Dentate Gyrus In order to establish whether the increase in the survival rate of newborn granule cells in the DG of Cdkl5 mutant mice after treatment (FIGS. 8A,C) translated also into restoration of total granule cell number, we evaluated the number of granule cells at the end of treatment. The granule cell layer of $Cdkl5^{-/Y}$ had a similar volume as that of $Cdkl5^{+/Y}$ mice but a reduced granule cell density and a reduced number of granule cells (FIGS. 9 A,C). In $Cdkl5^{-/Y}$ mice, treatment with NP-12 fully restored both granule cell density (FIG. 9 A) and total granule cell number (FIG. 9C), without affecting the volume of the granule cell layer (FIG. 9B).

Effect of Tideglusib (NP-12) Treatment on Dendritic Development

Figure 10A:
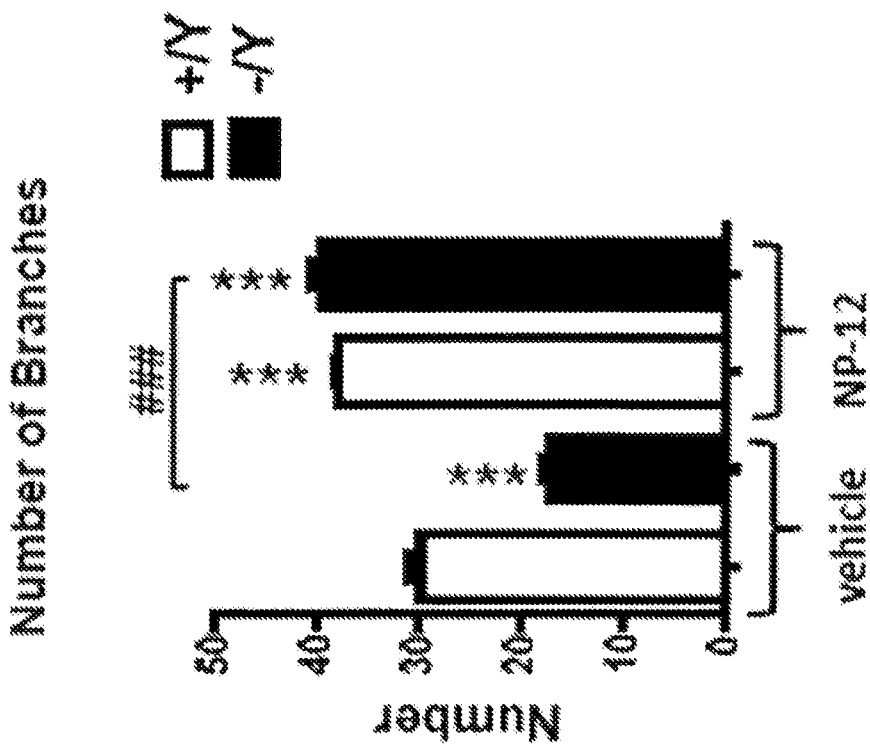
FIGS. 10A-10B show (A) the mean total dendritic length (left histogram) and mean number of dendritic segments (right histogram) of newborn granule cells of untreated (+/Y n=4, −/Y n=4) and treated (+/Y n=3, −/Y n=3) Cdkl5 male mice aged P45. (B) Quantification of the mean length (upper panel) and mean number (lower panel) of branches of the different orders in the same animals as in A. Values in A and B represent mean±SE. $*p<0.05$; $p<0.01$; $*p<0.001$ as compared to the untreated $Cdkl5^{+/Y}$ condition; $\#p<0.05$; $\#\#p<0.01$; $\#\#\#p<0.001$ as compared to the untreated $Cdkl5^{-/Y}$ samples (Duncan's test after ANOVA).
Figure 10A:
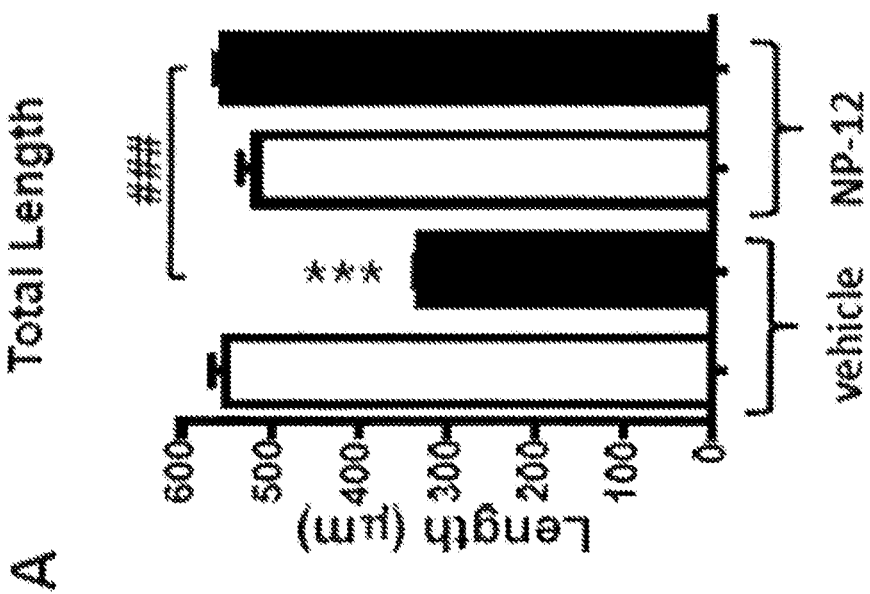
Figure 10B:
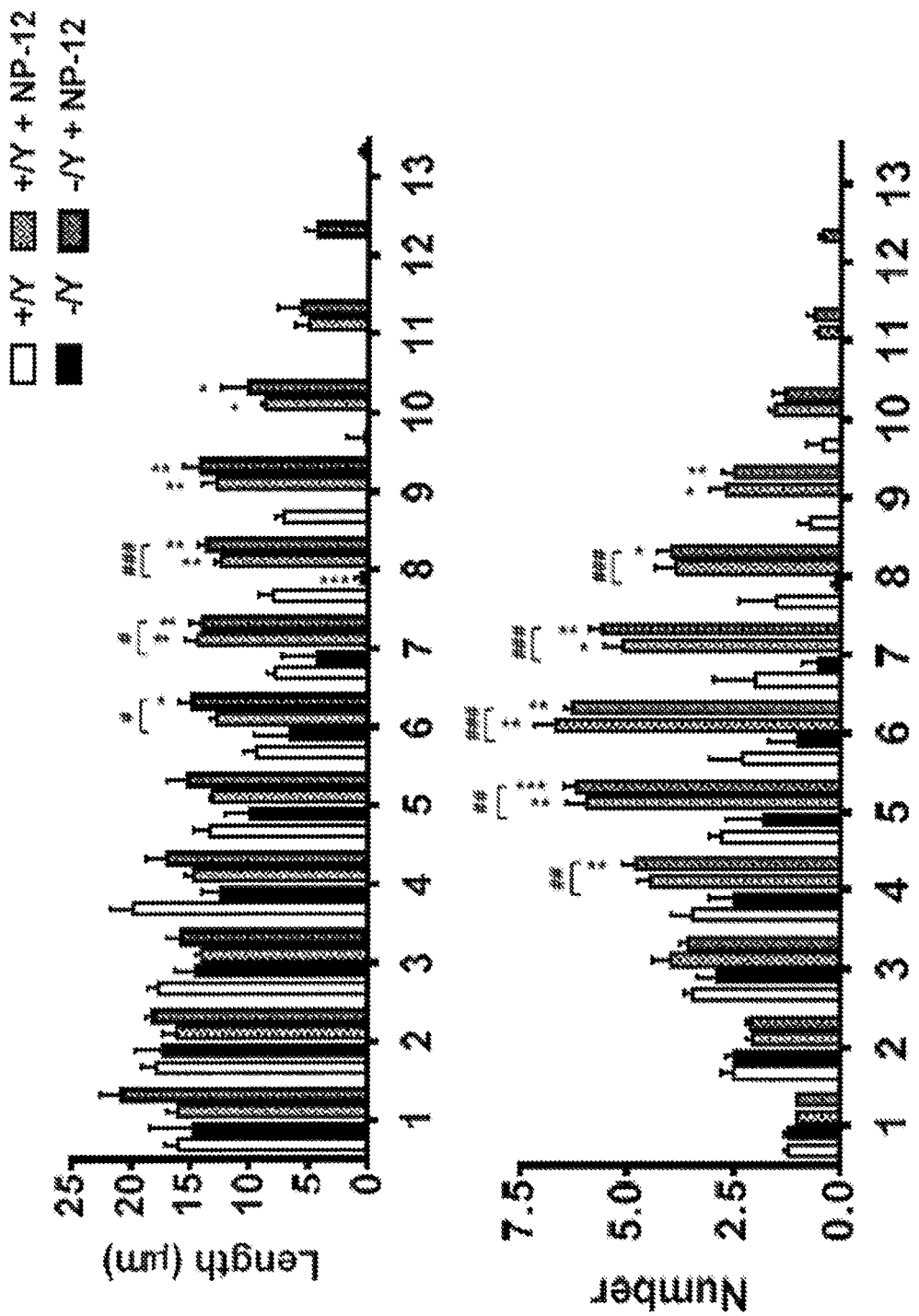

Loss of Cdkl5 negatively affects neuronal maturation and dendritic development. In order to evaluate the effect of NP-12 treatment on neuronal maturation, the dendritic morphology of granule neurons in sections immunostained with doublecortin DCX from treated and untreated Cdkl5 KO mice was examined. In untreated $Cdkl5^{-/Y}$ mice the dendritic tree had a reduced length and fewer branches compared to WT littermates (FIG. 10A). This dendritic hypotrophy is due to a reduced length and number of branches of higher order (FIG. 10B). In NP-12 treated $Cdkl5^{-/Y}$ mice there was an increase in both parameters that became similar or even greater than those of untreated $Cdkl5^{+/Y}$ mice (FIGS. 10 A,B). This evidence indicates that in $Cdkl5^{-/Y}$ mice treatment with NP-12 has a positive impact on dendritic development of newborn neurons. In order to establish the effects of NP-12 treatment also on the dendritic development of older granule cells, we evaluated Golgi-stained granule neurons located in the middle portion of the granule cell layer. $Cdkl5^{-/Y}$ mice had a shorter dendritic length and a reduced number of segments (FIGS. 11 A,B) compared to their WT counterparts. Both parameters were completely rescued by NP-12 treatment (FIG. 11 A,B). Taken together these results clearly indicate that NP-12 treatment has a positive effect on neuronal maturation in Cdkl5 mutant mice, by restoring dendritic architecture of newborn and older granule cells.

Effect of Tidegluisb Treatment on Spine Maturation

Figures 12A, 12B, 12C:
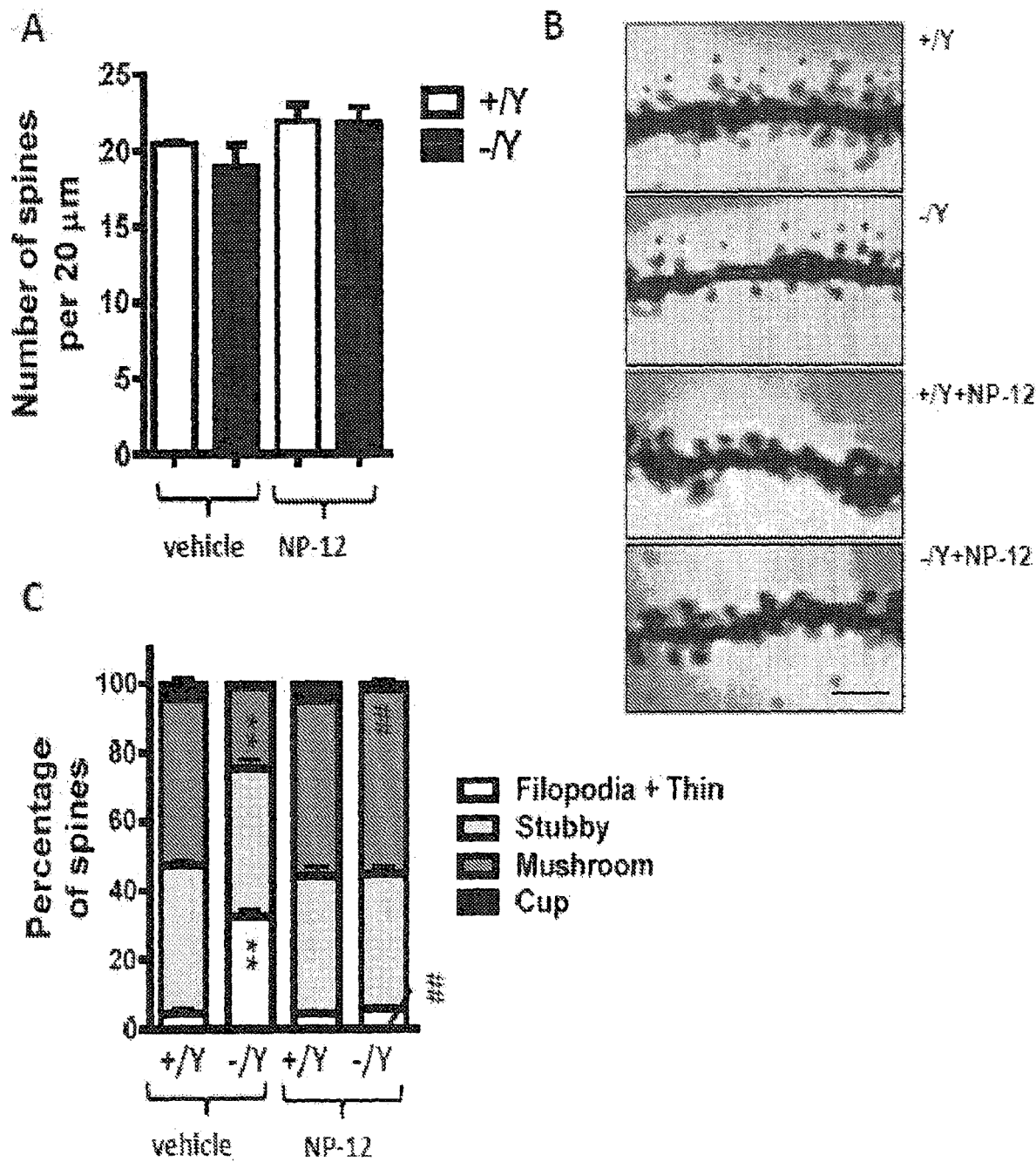
FIGS. 12A-12C demonstrate the (A) dendritic spine density of untreated (+/Y n=3, −/Y n=3) and treated (+/Y n=3, −/Y n=3) Cdkl5 male mice aged P45. (B) Images of Golgi-stained dendritic branches of granule cells of untreated and treated $Cdkl5^{+/Y}$ and $Cdkl5^{-/Y}$ male mice. Scale bar=10 µm. (C) Percentage of immature (filopodia+thin+stubby, red asterisks in B) and mature (mushroom+cup, blue asterisks in B) spines (see FIG. 17) in mice as in A. Values in A-C represent mean±SE. $**p<0.01$ as compared to the untreated $Cdkl5^{+/Y}$ condition; $\#\#p<0.01$ as compared to the untreated $Cdkl5^{-/Y}$ samples (Duncan's test after ANOVA).

Neurons receive their excitatory inputs through dendritic spines. Evidences in RTT subjects, as well as Mecp2 KO mice, show that spine density and morphology is impaired in RTT pathology. However, it is not known whether similar deficits exist in the brains of subjects carrying CDKL5 mutations. It has recently been shown that rodent neurons silenced for Cdkl5, iPSC-derived neurons from patients with CDKL5 mutation, as well as granule cells from Cdkl5 KO mice, exhibit deficits in dendritic spines. In order to evaluate the effect of NP-12 treatment on spines in Cdkl5 mutant mice, dendritic spine density and morphology/maturation of Golgi-stained granule neurons was examined. $Cdkl5^{-/Y}$ mice showed no difference in spine density compared to WT littermates (FIG. 12A). Treatment with NP-12 had no effect on spine density (FIG. 12A).

$Cdkl5^{-/Y}$ mice granule neurons show dendritic spine protrusions that are significantly thinner when compared with controls and that exhibit a filopodia-like morphology, indicating that CDKL5 is involved in correct dendritic spine morphogenesis. Similar results were obtained also by Della Sala and colleagues. By using in-vivo two-photon imaging, they found that dendritic spines exhibit impaired structural plasticity in Cdkl5 KO mice. In order to evaluate the effect of NP-12 treatment on spine maturation, spine morphology in Golgi-stained granule cells at the end of treatment was evaluated. Cdkl5 KO mice show a higher percentage of immature spines (thin+filopodia+stubby, FIG. 12B: red asterisks) compared to their WT littermates (FIG. 12B), with a corresponding reduction in the number of mature spines (mushroom+cup, FIG. 12B: blue asterisks). Differences in spine shape morphology were completely restored by treatment with the GSK3β inhibitor NP-12, suggesting that G538 inhibition had positive effects also on dendritic spine maturation.

Effect of Tideglusib (NP-12) Treatment on Hippocampal Connectivity

Reduction in connectivity is the counterpart of the severe dendritic hypotrophy that characterizes $Cdkl5^{-/Y}$ mice. Since dendritic spine structure is fundamental for synaptic contact maintenance, in hippocampal sections from treated and untreated mice, we evaluated the immunoreactivity for synaptophysin (SYN, also known as p38), an integral membrane glycoprotein of synaptic vesicles that is a specific marker of presynaptic terminals, and the postsynaptic density protein-95 (PSD-95), a marker of postsynaptic sites. In untreated $Cdkl5^{-/Y}$ mice the optical density (OD) of SYN (FIG. 13A) was significantly lower than in control littermates. In parallel with the reduction of SYN immunoreactivity, in Cdkl5 mutant mice there was a reduction in the immunoreactivity for PSD-95 (FIG. 13B). In $Cdkl5^{-/Y}$ mice treated with NP-12 these defects were fully rescued (FIGS. 13A, B), suggesting that the positive impact of NP-12 treatment on dendritic development is paralleled by restoration of the input to the granule. In order to establish whether the observed differences in immunoreactivity were attributable to different levels of synaptic proteins per synapse or to differences in the number of synapses, the density of individual puncta exhibiting either SYN or PSD-95 immunoreactivity was additionally evaluated. While untreated $Cdkl5^{-/Y}$ mice had fewer SYN and PSD-95 puncta (FIGS. 13 C,F), in NP-12 treated animals the density of both immune puncta were completely restored (FIGS. 13C,F), suggesting that treatment with NP-12 restores hippocampal synapse development in Cdkl5 KO mice.

Effect of Tideglusib (NP-12) Treatment on Hippocampus Dependent Memory

Figures 14A, 14B:
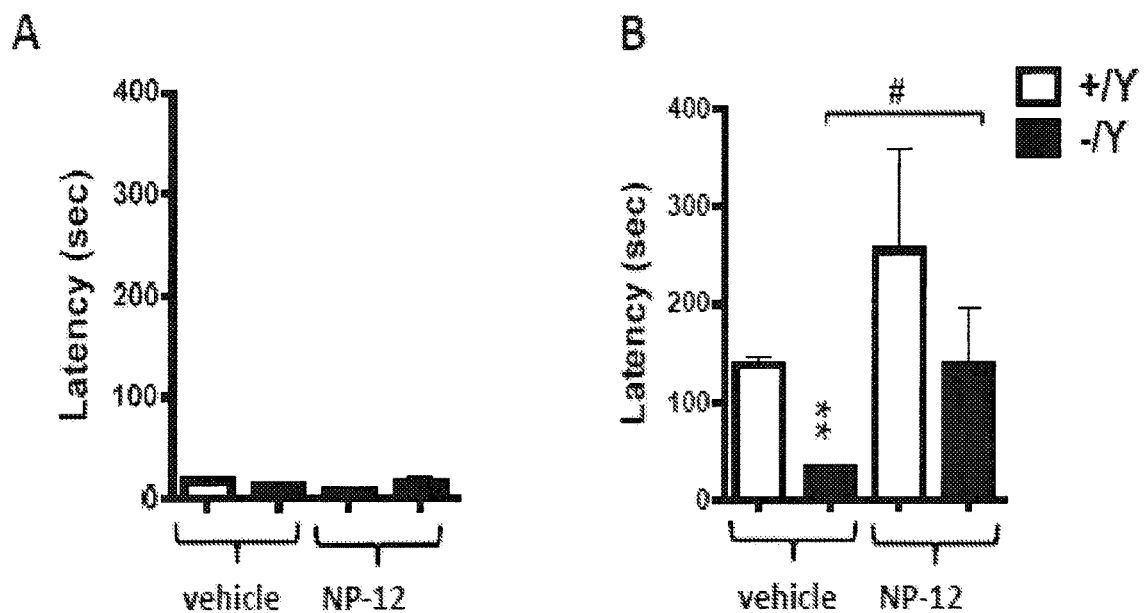
FIGS. 14A-14B demonstrate the results from a (A,B) passive avoidance test (PA) on untreated (+/Y n=12, −/Y n=12) and treated (+/Y n=3, −/Y n=6) Cdkl5 male mice at the end of treatment. Graphs show the latency time for entering the dark compartment on the first day (A) and on the second day (B) of the behavioral procedure. Values represent mean±SE. $**p<0.01$ as compared to the untreated $Cdkl5^{+/Y}$ condition; $\#p<0.05$ as compared to the untreated $Cdkl5^{-/Y}$ condition. (Duncan's test after ANOVA).

Cdkl5 impairs hippocampus-dependent memory. In order to establish whether treatment with NP-12 could ameliorate hippocampus-dependent memory deficits in mice, at the end of treatment mice were subjected to the Passive Avoidance (PA) test. The Passive Avoidance task is a widely used fear-aggravated test, which allows to evaluate memory performance in rodent models of central nervous system disorders. In this test an animal is conditioned with a single aversive stimulus (such as a foot-shock) and later tested for recollection of that experience. FIGS. 14A and B report the latency time to enter the dark compartment on the first day and on the second day (test). On the first day, all groups showed similar step-through latencies (FIG. 14A). After 24 hours (second day), animals were re-placed in the test apparatus to test their memory. Untreated Cdkl5$^{-/Y}$ mice were severely impaired in this task, as shown by a reduced latency to enter the dark compartment in comparison with Cdkl5$^{+/Y}$ mice (FIG. 14B). In NP-12 treated Cdkl5$^{-/Y}$ mice the latency underwent an increase and there was no significant difference in comparison to untreated Cdkl5$^{+/Y}$ mice (FIG. 14B). Evaluation of memory performance with the PA test shows that treated Cdkl5$^{-/Y}$ mice still exhibit a memory performance similar to that of untreated Cdkl5$^{+/Y}$ mice (FIG. 14B), indicating that NP-12 treatment has positive effects also on memory deficits in Cdkl5 mutant mice.

Example 2

Figures 18A, 18B:
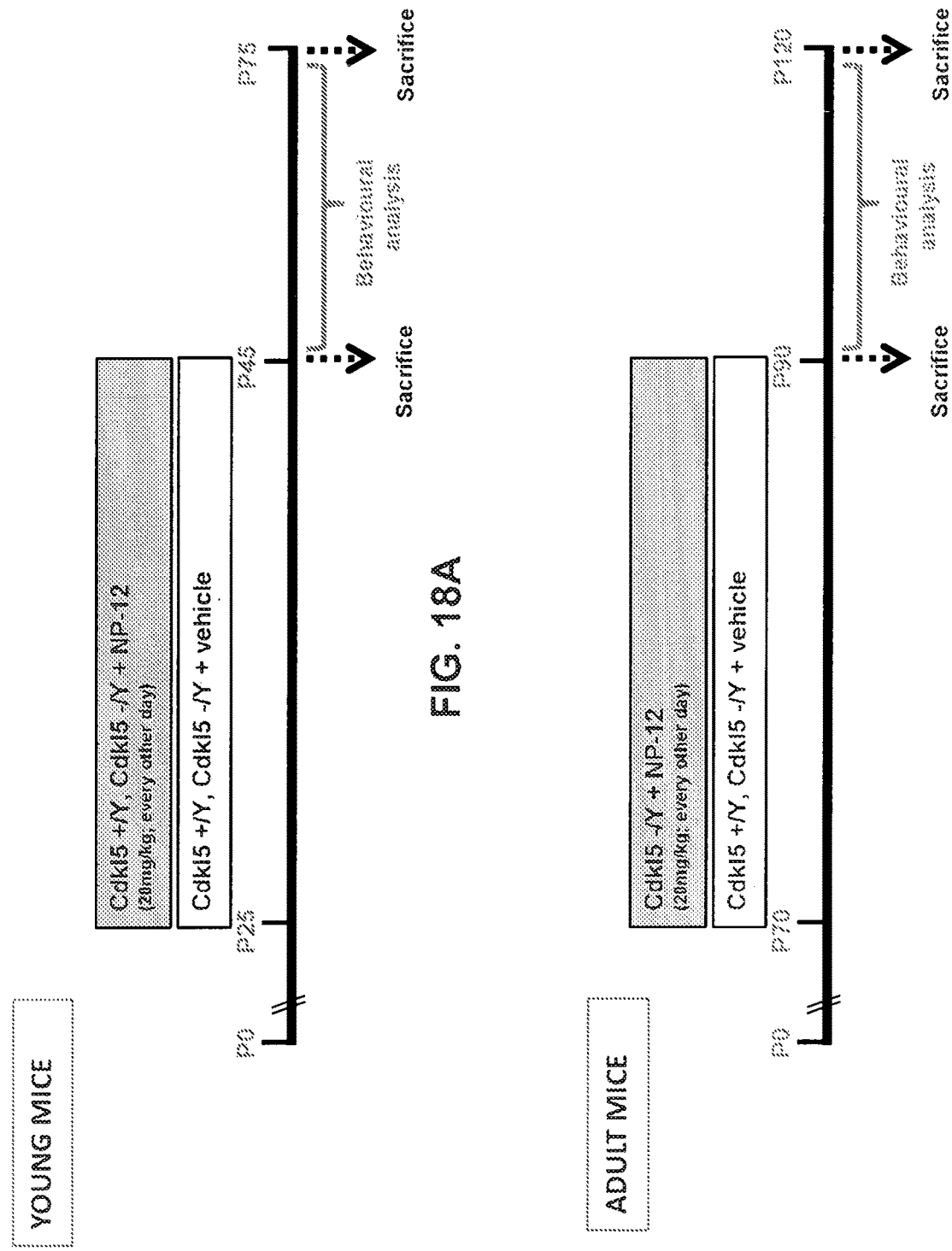
FIGS. 18A-18B depict the experimental protocol for evaluating the effect of tideglusib in young and adult mice.
Figures 19A, 19B, 19C:
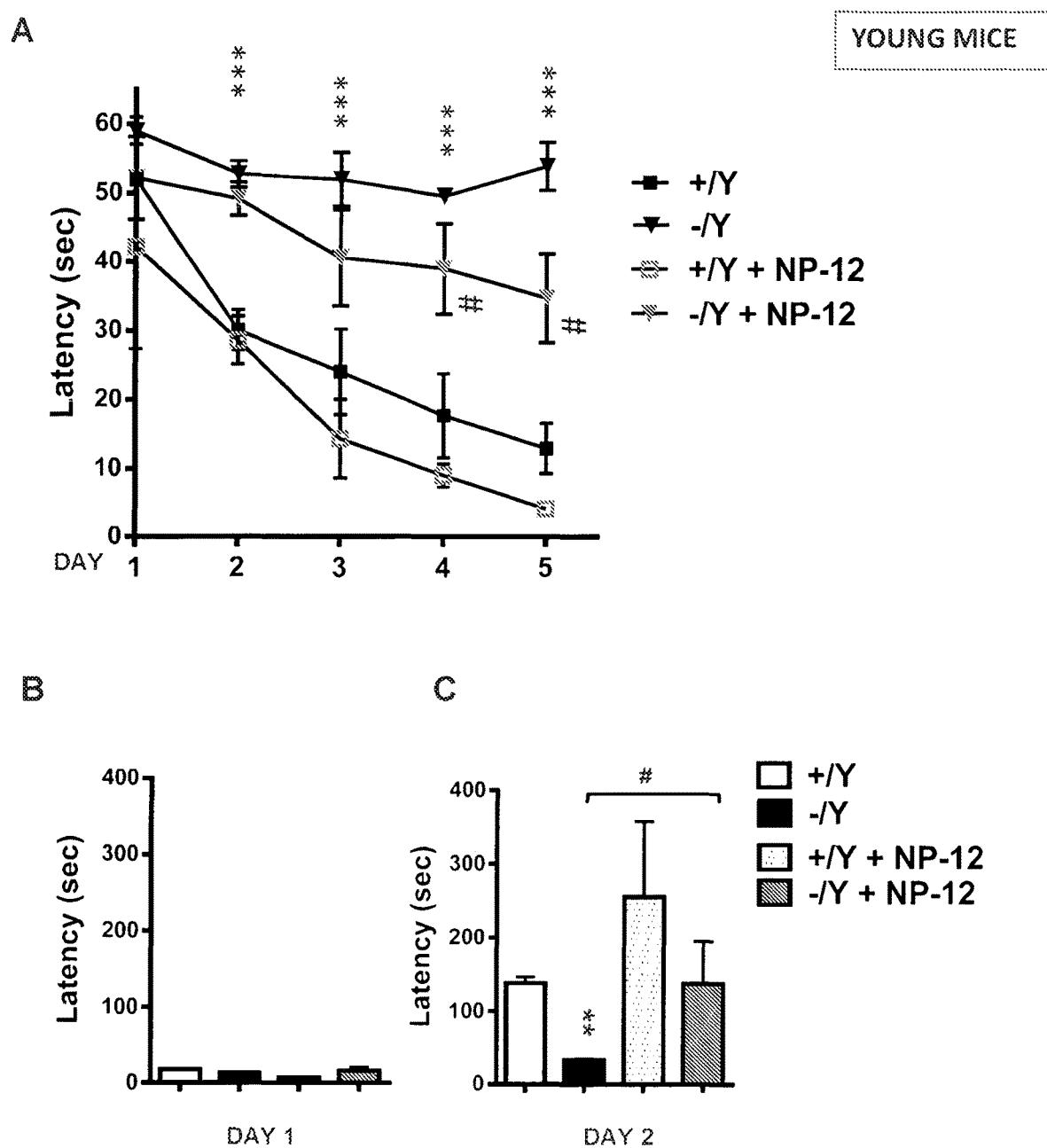

The effects of age on GSK3β activity and NP-12 treatment were examined. Phosphorylated (inactive) and unphosphorylated (active) GSK3β was examined in wild-type (+/Y) and CDKL5 KO (–/Y) male mice of different ages. The results are demonstrated in FIGS. 17A-17C. The effect of NP-12 was then examined in wild-type (+/Y) and CDKL5 KO (–/Y) male mice of different ages. The experimental protocols are depicted in FIGS. 18A-18B. Spatial learning was assessed with the Morris water maze in untreated and treated wild-type and CDKL5 male mice of different ages. The results are demonstrated in FIGS. 19A-19C and 20.

Example 3

Figures 21A, 21B:
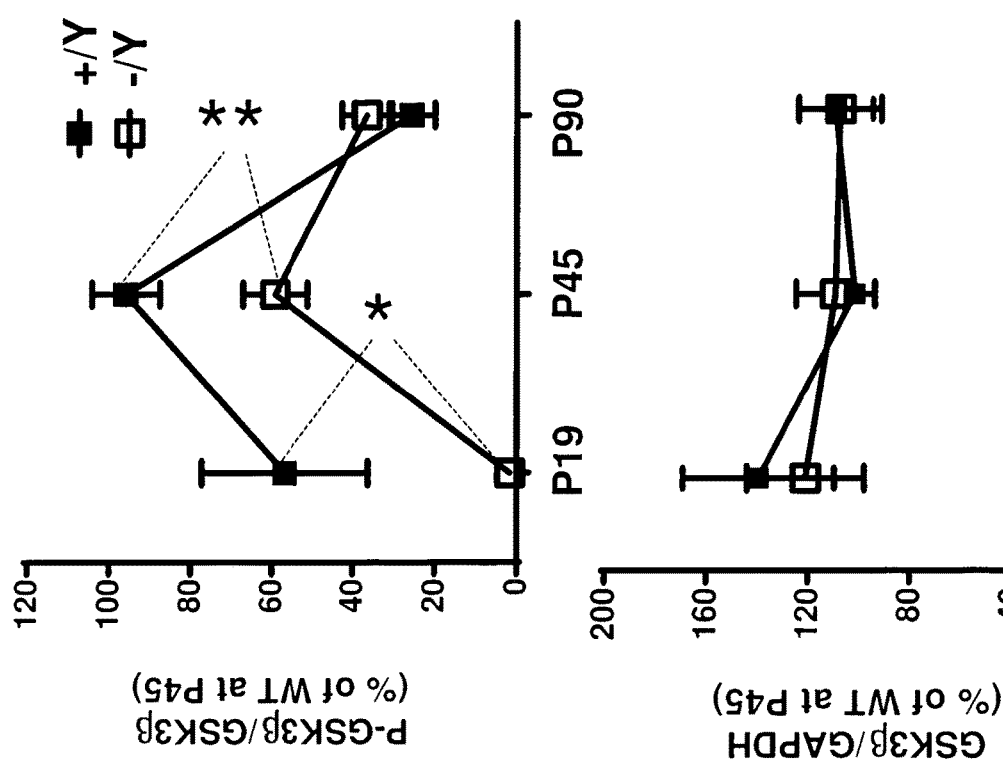
FIGS. 21A-21B show graphs demonstrating the results from Western Blot analysis of P-GSK3β-Ser9 (A) and GSK3β(B) levels in the hippocampal formation of wildtype (+/Y) and Cdkl5 (−/Y) male mice at different ages (P19, P45, P90).
Figure 22A:
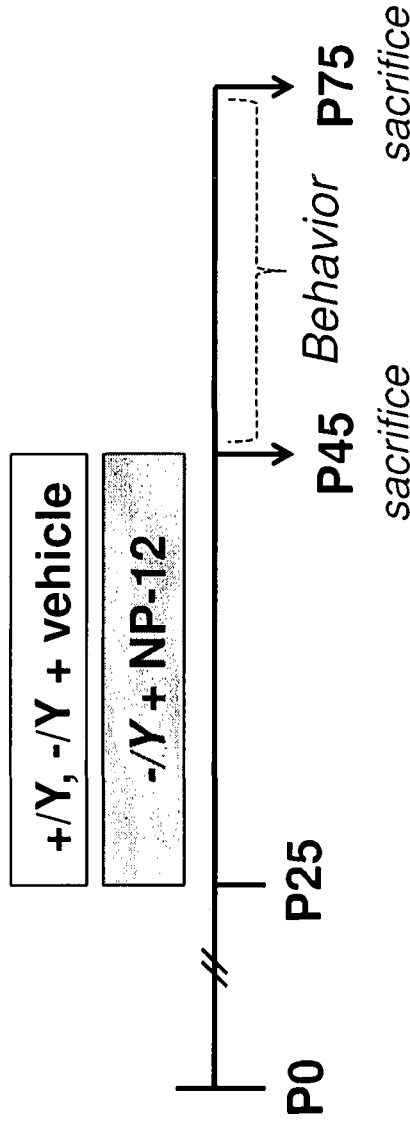
FIGS. 22A-22B show an experimental protocol for evaluating the effect of NP-12 in juvenile and adult mice. Starting from postnatal day 25 (P25) for juvenile mice (A) or postnatal day 90 (P90) for adult mice (B), $Cdkl5^{+/Y}$ and $Cdkl5^{-/Y}$ male mice were treated with vehicle or NP-12, administered by subcutaneous injection every other day for 20 days. Animals were sacrificed after the last injection (on P45 and P110 for juvenile and adult mice, respectively) or were behaviorally tested. Abbreviations: +/Y: wildtype male mice; −/Y: Cdkl5 KO male mice; P, postnatal day.
Figure 22B:
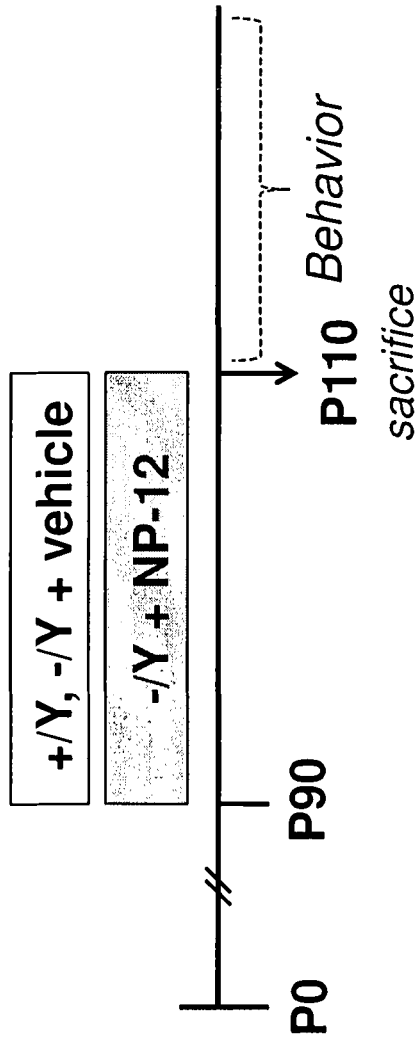

The effects of age on GSK3β activity and NP-12 treatment were examined. Phosphorylated (inactive) and unphosphorylated (active) GSK3β was examined in wild-type (+/Y) and CDKL5 KO (–/Y) male mice of different ages. The results are demonstrated in FIGS. 21A-21B. The effect of NP-12 was then examined in wild-type (+/Y) and CDKL5 KO (–/Y) male mice of different ages. The experimental protocols are depicted in FIGS. 22A-22B.

Figure 23A:
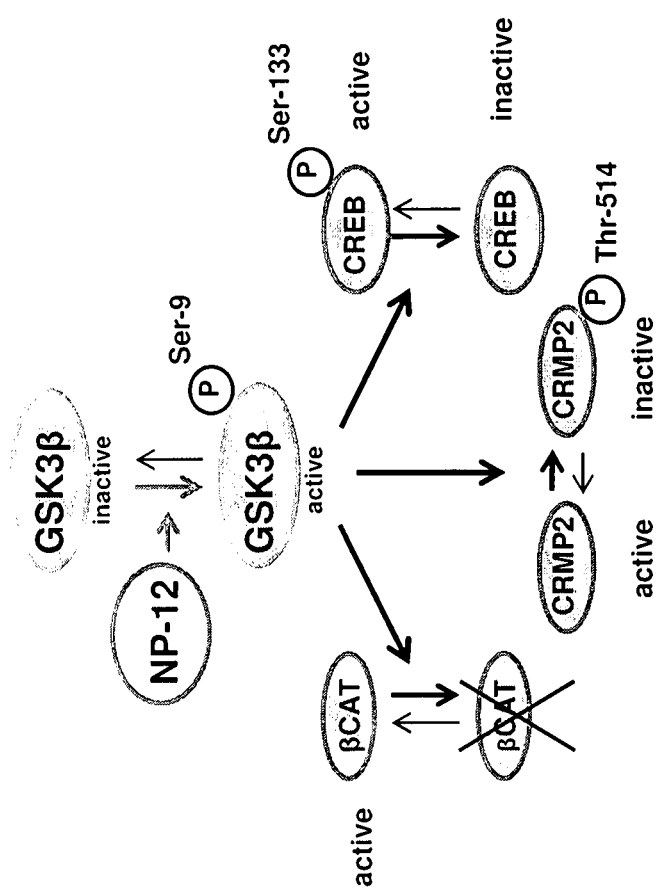
FIG. 23A shows a diagram of GSK3β and its downstream targets.
Figure 23B:
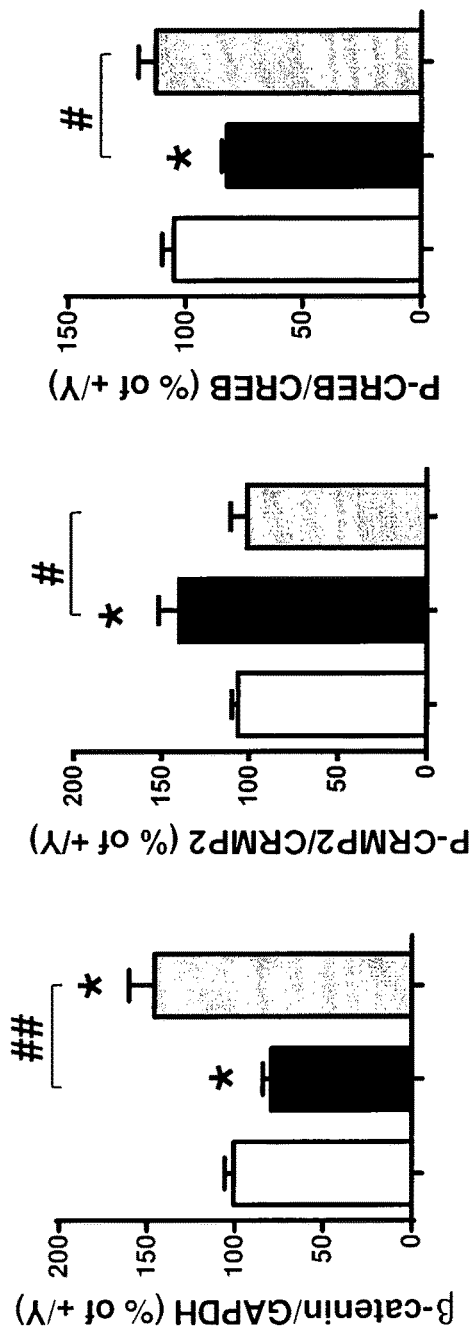
FIGS. 23B-23C show the results from Western Blot analysis. of β-catenin, P-CRMP2 Thr-514, and P-CREB Ser-133 levels in the hippocampus of vehicle treated and NP-12 treated Cdkl5+/Y and −/Y male mice aged P45 (B) and P110 (C). Data are expressed as percentage of vehicle treated Cdkl5+/Y mice of the same age. Values are represented as means±SE. $*p<0.05$, $p<0.01$, $*p<0.001$ as compared to the vehicle-treated Cdkl5 +/Y condition; $\#p<0.05$; $\#\#p<0.01$, $\#\#\#p<0.001$ as compared to the vehicle-treated Cdkl5 −/Y condition (Duncan's test after ANOVA).
Figure 23C:
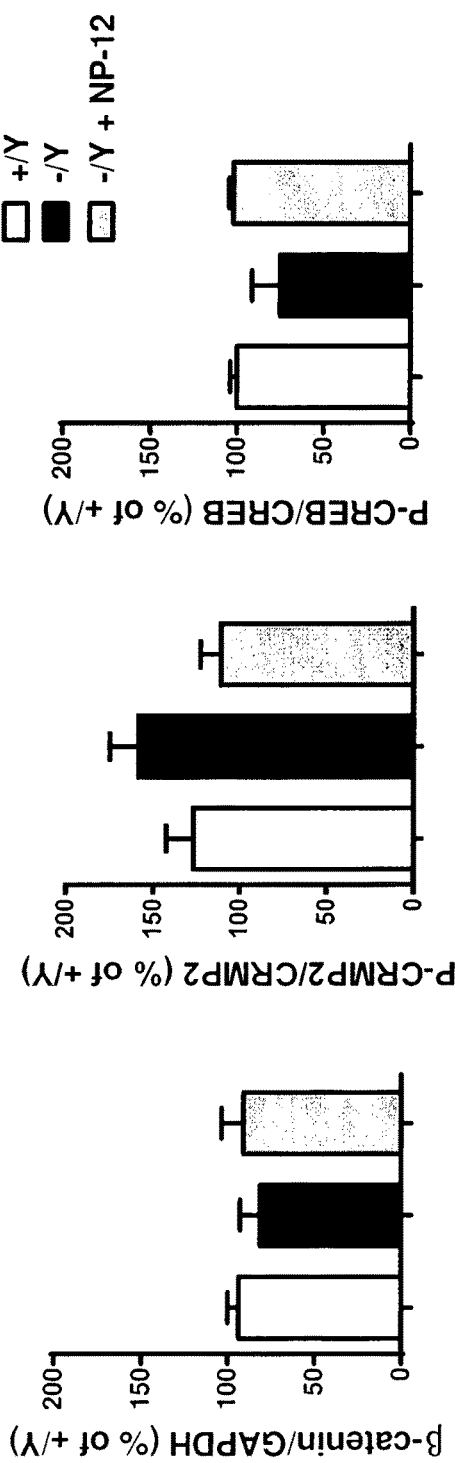

A diagram of GSK3β and its downstream targets is depicted in FIG. 23A. The effects of treatment with NP-12 on GSK3β-dependent targets was evaluated and the results are demonstrated in FIGS. 23B-23C. As can be seen from FIGS. 23B-23C, treatment with NP-12 restores GSK3β-dependent targets in juvenile, but not adult, CDKL5 KO mice.

Figure 24A:
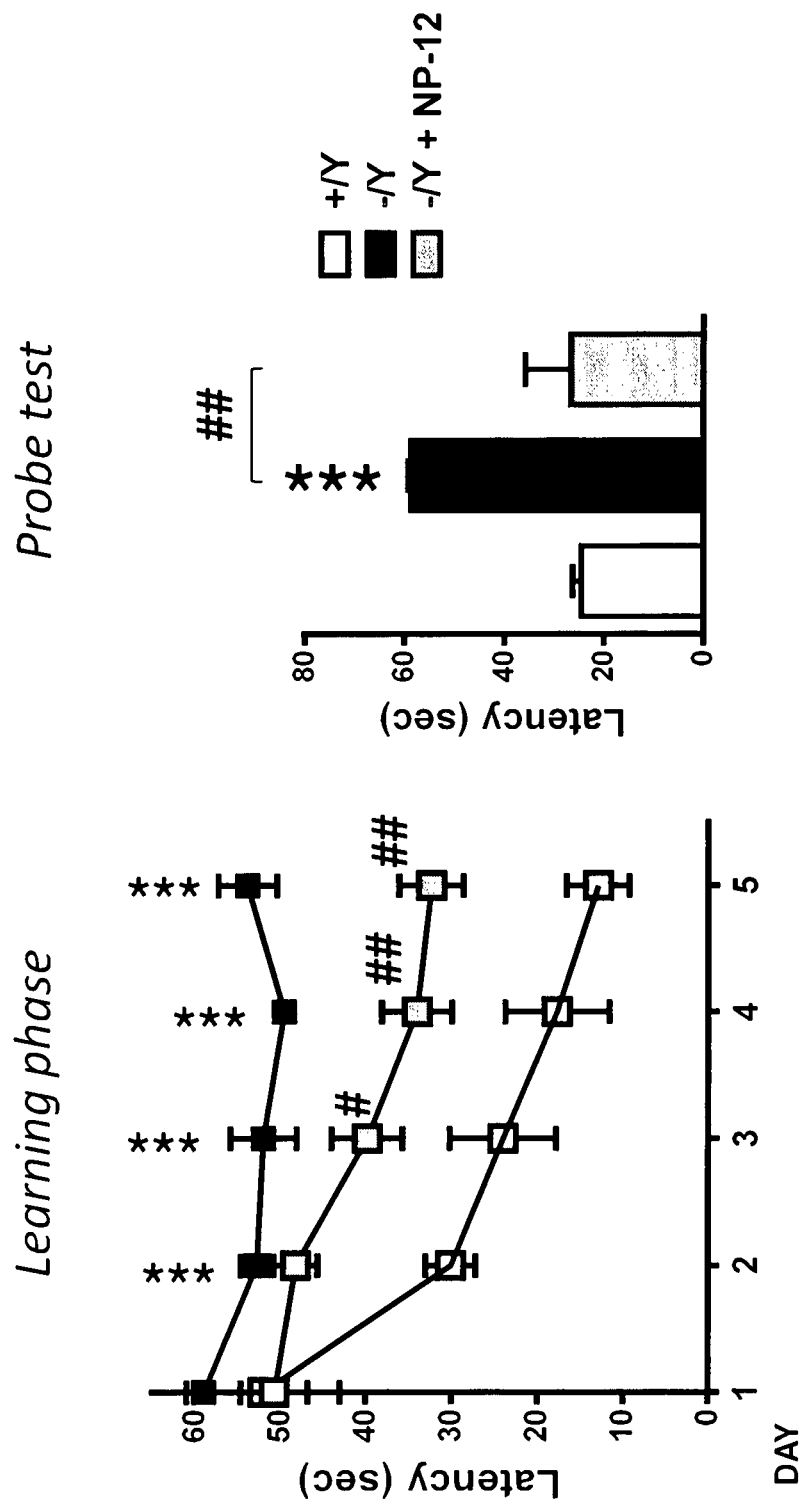
FIGS. 24A-24C show the results from spatial learning, memory and passive avoidance tests of vehicle treated and NP-12 treated Cdkl5+/Y and −/Y male mice. Spatial learning and memory (probe test) assessed with the Morris water maze in vehicle treated and NP-12 treated Cdkl5+/Y and −/Y male mice aged P45 (A) and aged P110 (B). Passive avoidance test (PA) on vehicle treated and NP-12 treated Cdkl5+/Y and −/Y male mice aged P45 (C). Graphs show the latency time to enter the dark compartment on the first day and on the second day of the behavioral procedure. Values are represented as means±SE. $*p<0.05$, $p<0.01$, $*p<0.001$ as compared to the vehicle-treated Cdkl5+/Y condition; $\#p<0.05$; $\#\#p<0.01$, $\#\#\#p<0.001$ as compared to the vehicle-treated Cdkl5−/Y condition (Duncan's test after ANOVA).
Figure 24B:
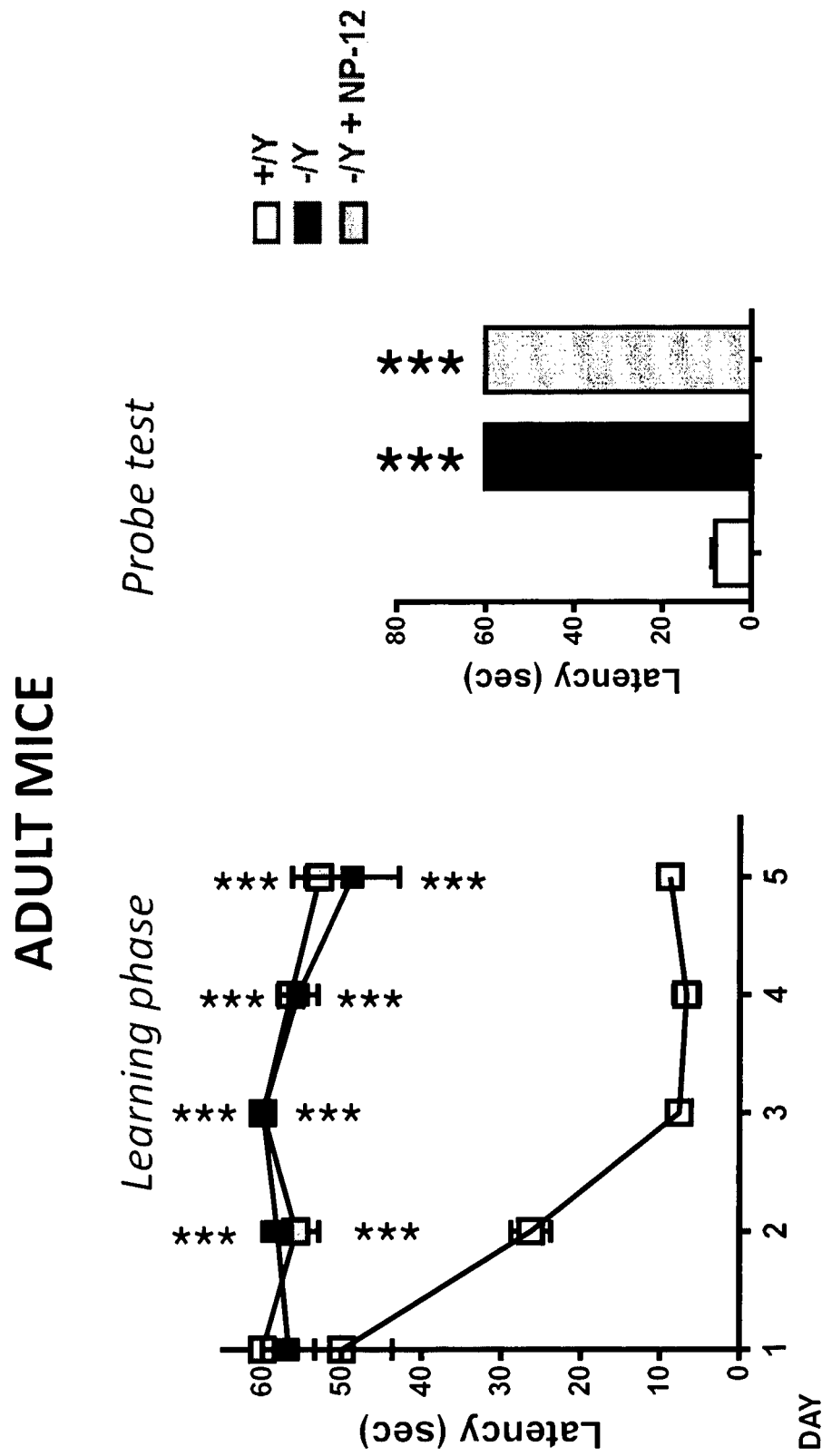
Figure 24C:
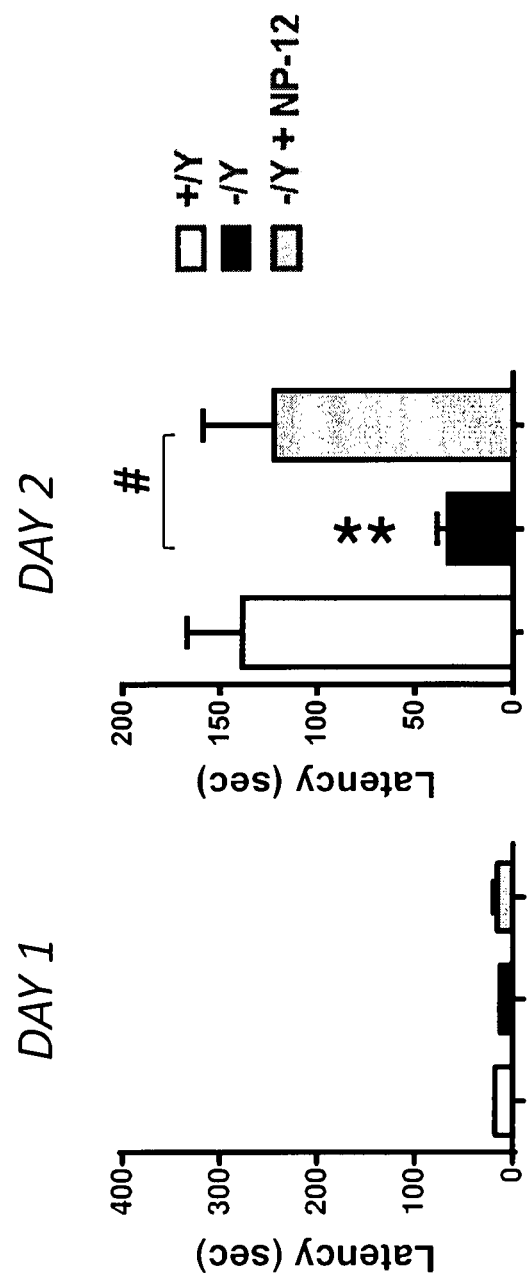
Figures 25A, 25B:
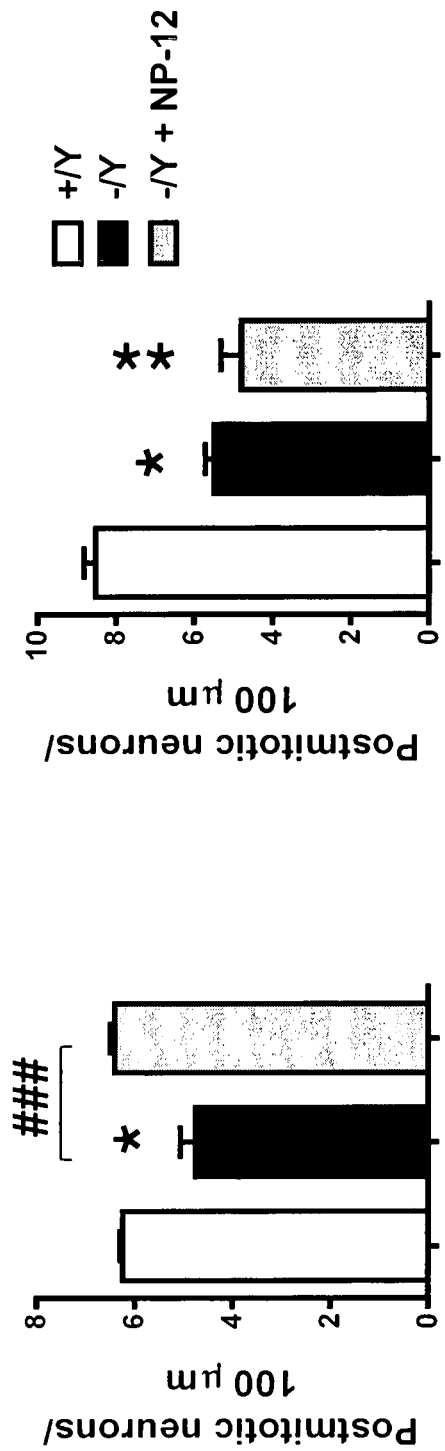
FIGS. 25A-25B show the quantification of the number of DCX-positive postmitotic neurons in the dentate gyrus of vehicle treated and NP-12 treated Cdkl5+/Y and −/Y male mice aged P45 (A) and aged P110 (B). Data are expressed as number of cells/100 μm. Values are represented as means±SE. $*p<0.05$, $p<0.01$, $*p<0.001$ as compared to the vehicle-treated Cdkl5+/Y condition; $\#p<0.05$; $\#\#p<0.01$, $\#\#\#p<0.001$ as compared to the vehicle-treated Cdkl5 −/Y condition (Duncan's test after ANOVA).
Figures 26A, 26B:
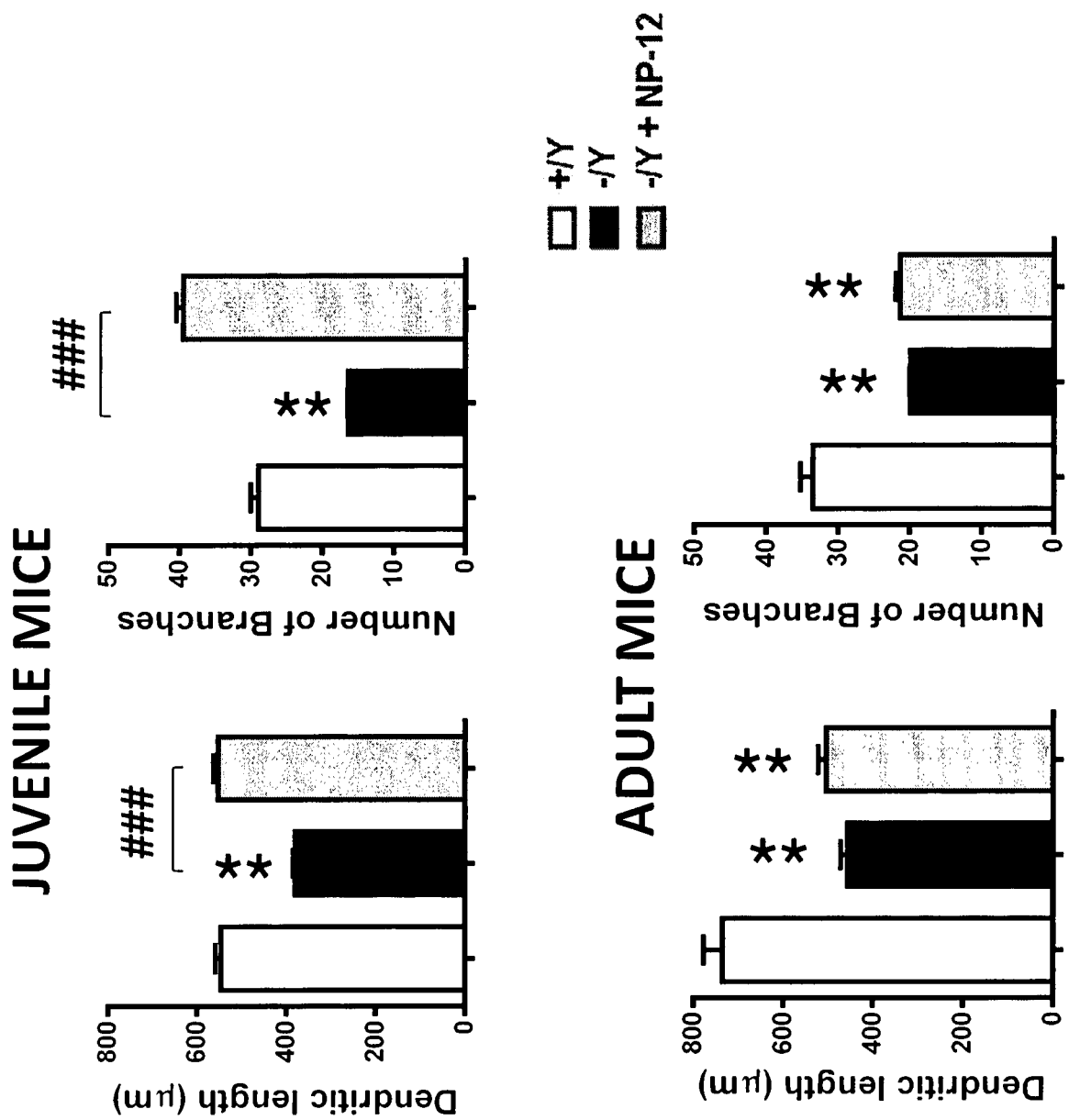
FIGS. 26A-26B show the mean total dendritic length and mean number of dendritic branches of newborn granule cells of vehicle treated and NP-12 treated Cdkl5+/Y and −/Y male mice aged P45 (A) and aged P110 (B).
Figure 26C:
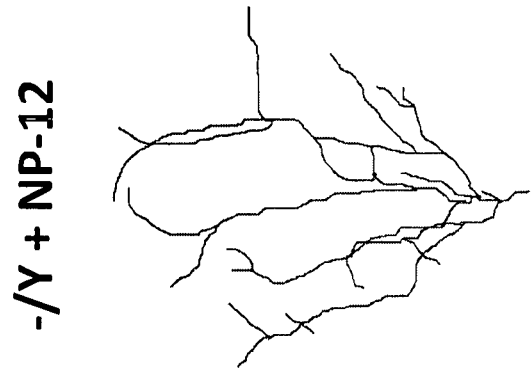
FIG. 26C shows examples of the reconstructed dendritic tree of granule cells of mice as in FIG. 25A aged P45.
Figure 26C:
Figure 26C:
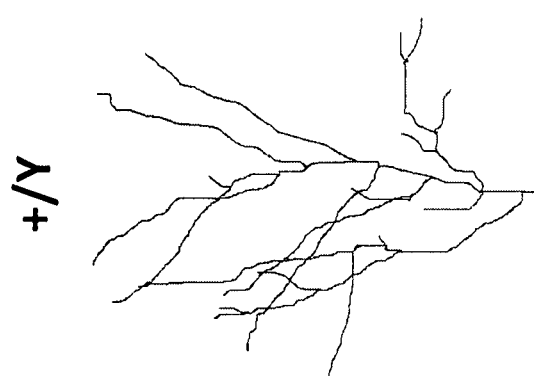

The effects of treatment with NP-12 on hippocampus-dependent learning and memory was evaluated and the results are demonstrated in FIGS. 24A-24C. As can be seen from FIGS. 24B-24C, treatment with NP-12 corrects hippocampus-dependent behavior defects in juvenile, but not adult, CDKL5 KO mice.

The effects of treatment with NP-12 on neuronal survival and maturation was evaluated and the results are demonstrated in FIGS. 25A-24B and 26A-26C. As can be seen from FIGS. 25A-25B and 26A-26C, treatment with NP-12 restores neuronal survival and maturation in juvenile, but not adult, CDKL5 KO mice.

Figure 27A:
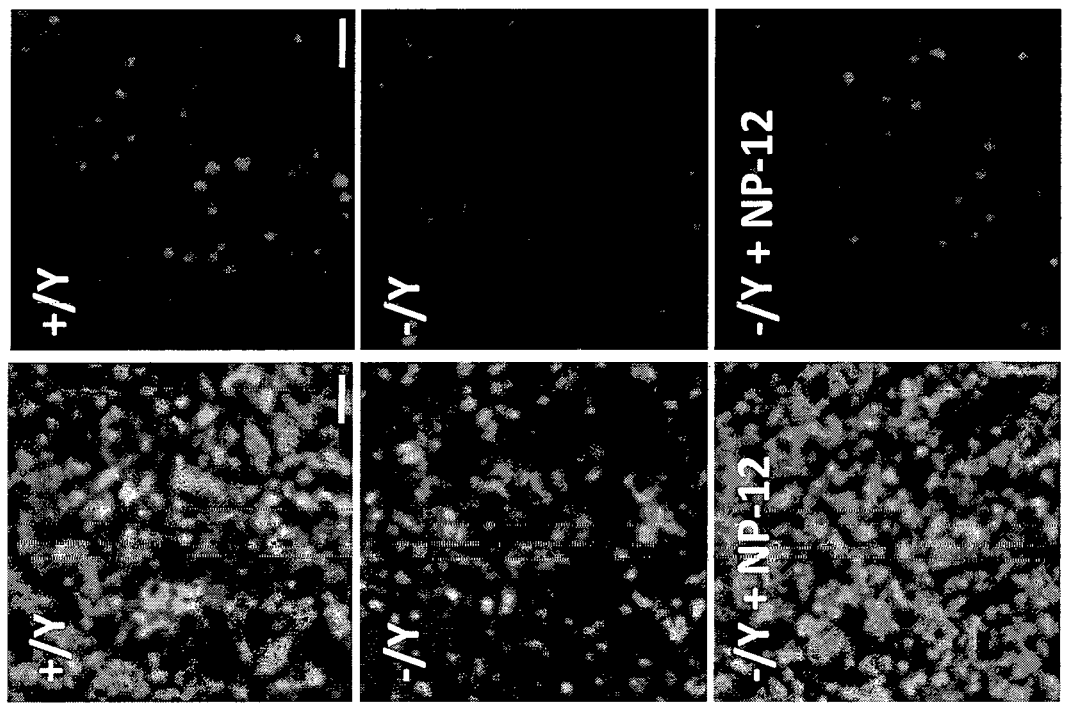
FIG. 27A shows representative images of sections processed for SYN (left row) and PSD-95 (right row) immunofluorescence from the dentate gyrus (DG) of vehicle treated and NP-12 treated Cdkl5+/Y and −/Y male mice aged P45.
Figure 27C:
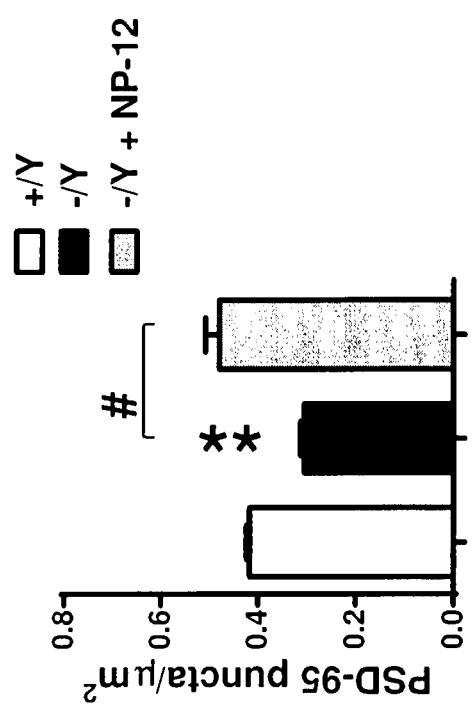
FIGS. 27B-27C show the number of puncta per $\mu m^2$ exhibiting SYN (B) and PSD-95 (C) immunoreactivity in the DG of mice as in FIG. 25A. Values are represented as means±SE. $*p<0.05$, $p<0.01$, $*p<0.001$ as compared to the vehicle-treated Cdkl5+/Y condition; $\#p<0.05$; $\#\#p<0.01$, $\#\#\#p<0.001$ as compared to the vehicle-treated Cdkl5 −/Y condition (Duncan's test after ANOVA).
Figure 27B:
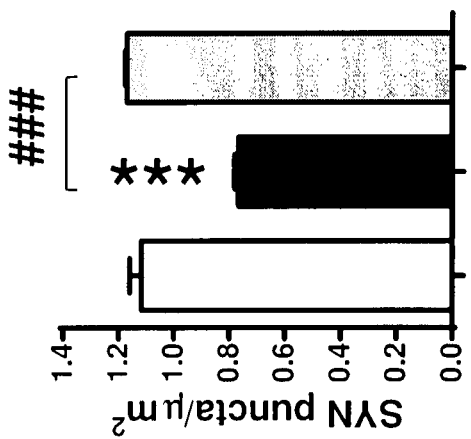

The effects of treatment with NP-12 on synapse development was evaluated and the results are demonstrated in FIGS. 27A-27C. As can be seen from FIGS. 27A-27C, treatment with NP-12 restores synapse development in juvenile CDKL5 KO mice.

We claim:

1. A method of treating a CDKL5 deficiency in a subject in need thereof, the method comprising:
   administering an amount of tideglusib to the subject in need thereof.

2. The method of claim 1, wherein the amount is an amount effective to increase the dendritic length of newborn granule cells as compared to an untreated control subject or population.

3. The method of claim 1, wherein the amount is an amount effective to increase the number of dendrite branches of neuronal cells as compared to an untreated control subject or population.

4. The method of claim 1, wherein the amount is an amount effective to increase granule cell connectivity as compared to an untreated control subject or population.

5. The method of claim 1, wherein the amount is an amount effective to reduce at least one symptom of the CDKL5 deficiency.

6. The method of claim 1, wherein the subject is a juvenile.

7. The method of claim 1, wherein the amount ranges from about 2 mg/kg bodyweight to about 50 mg/kg bodyweight.

8. The method of claim 1, wherein the amount is the least amount effective to increase the dendritic length of newborn granule cells as compared to an untreated control subject or population.

9. The method of claim 1, wherein the amount is the least amount effective to increase the number of dendrite branches of neuronal cells as compared to an untreated control subject or population.

10. The method of claim 1, wherein the amount is the least amount effective to increase granule cell connectivity as compared to an untreated control subject or population.

11. The method of claim 1, wherein the amount is the least amount effective to reduce at least one symptom of the CDKL5 deficiency.

12. The method of claim 1, wherein the least effective amount ranges from about 2 mg/kg bodyweight to 50 about mg/kg bodyweight.

13. The method of claim 1, wherein the amount is delivered orally, intravenously, subcutaneously, intraventricularly, or intramuscularly.

14. The method of claim 1, wherein the tideglusib is included in a pharmaceutical formulation.

15. The method of claim 1, wherein the tideglusib is administered in at least two dosages administered sequentially.

16. The method of claim 1, wherein the tideglusib is administered every other day.

* * * * *